(12) United States Patent
Avitall

(10) Patent No.: US 6,308,091 B1
(45) Date of Patent: Oct. 23, 2001

(54) MAPPING AND ABLATION CATHETER SYSTEM

(76) Inventor: Boaz Avitall, 4868 N. Ardmore Ave., Milwaukee, WI (US) 53217

(*) Notice: Subject to any disclaimer, the term of this patent is extended or adjusted under 35 U.S.C. 154(b) by 0 days.

(21) Appl. No.: 09/629,208

(22) Filed: Jul. 31, 2000

Related U.S. Application Data

(60) Continuation of application No. 09/154,854, filed on Sep. 17, 1998, now Pat. No. 6,138,043, which is a division of application No. 08/968,159, filed on Nov. 12, 1997, now Pat. No. 5,842,984, which is a division of application No. 08/593,660, filed on Jan. 29, 1996, now Pat. No. 5,730,127, which is a continuation-in-part of application No. 08/487,492, filed on Jun. 19, 1995, now Pat. No. 5,687,723, which is a continuation-in-part of application No. 08/161,920, filed on Dec. 3, 1993, now Pat. No. 5,487,385.

(51) Int. Cl.[7] ............................... A61B 5/04; A61N 1/05
(52) U.S. Cl. ........................... 600/374; 606/41; 607/122
(58) Field of Search ..................... 600/373–375, 600/377, 387; 606/41, 47; 607/98, 99, 101, 122, 125, 126

(56) References Cited

U.S. PATENT DOCUMENTS

| | | |
|---|---|---|
| 4,493,320 | 1/1985 | Treat . |
| 4,660,571 | 4/1987 | Hess et al. . |
| 4,664,120 | 5/1987 | Hess . |
| 4,690,155 | 9/1987 | Hess . |
| 4,699,147 | 10/1987 | Chilson et al. . |
| 5,010,894 | 4/1991 | Edhag . |
| 5,156,151 | 10/1992 | Imran . |
| 5,228,442 | 7/1993 | Imran . |
| 5,231,995 | 8/1993 | Desai . |
| 5,263,493 | 11/1993 | Avitall . |
| 5,293,869 | 3/1994 | Edwards et al. . |
| 5,324,284 | 6/1994 | Imran . |
| 5,370,679 | 12/1994 | Atlee, III . |
| 5,427,119 | 6/1995 | Swartz . |
| 5,476,495 | 12/1995 | Kordis et al. . |
| 5,482,037 | 1/1996 | Borghi . |
| 5,487,385 * | 1/1996 | Avitall .................................. 600/374 |
| 5,499,981 | 3/1996 | Kordis . |
| 5,687,723 * | 11/1997 | Avitall .................................. 600/374 |
| 5,730,127 * | 3/1998 | Avitall .................................. 600/374 |
| 5,842,984 * | 12/1998 | Avitall .................................. 600/374 |

OTHER PUBLICATIONS

Avitall, Boaz, et al, "Physics and Engineering of Transcatheter Cardiac Tissue Ablation", *JACC*, vol. 22, No. 3, Sep. 1993, 921–32.

* cited by examiner

*Primary Examiner*—Jeffrey R. Jastrzab
(74) *Attorney, Agent, or Firm*—Nikolai & Mersereau, P.A.

(57) ABSTRACT

A recording and ablation catheter method and system for creating linear lesions in an atrial or other chamber of a heart is disclosed which includes an array of readily controlled electroded arcuate distal working catheter shapes that are easily deployed to contact the inner wall surface of the right atrial cardiac chamber in a manner that enables easy recording and mapping of impulses and thereafter facilitates sustained contact so that linear lesions can be produced from an array of mapping and ablation electrode devices serially spaced along the working catheter shape.

11 Claims, 21 Drawing Sheets

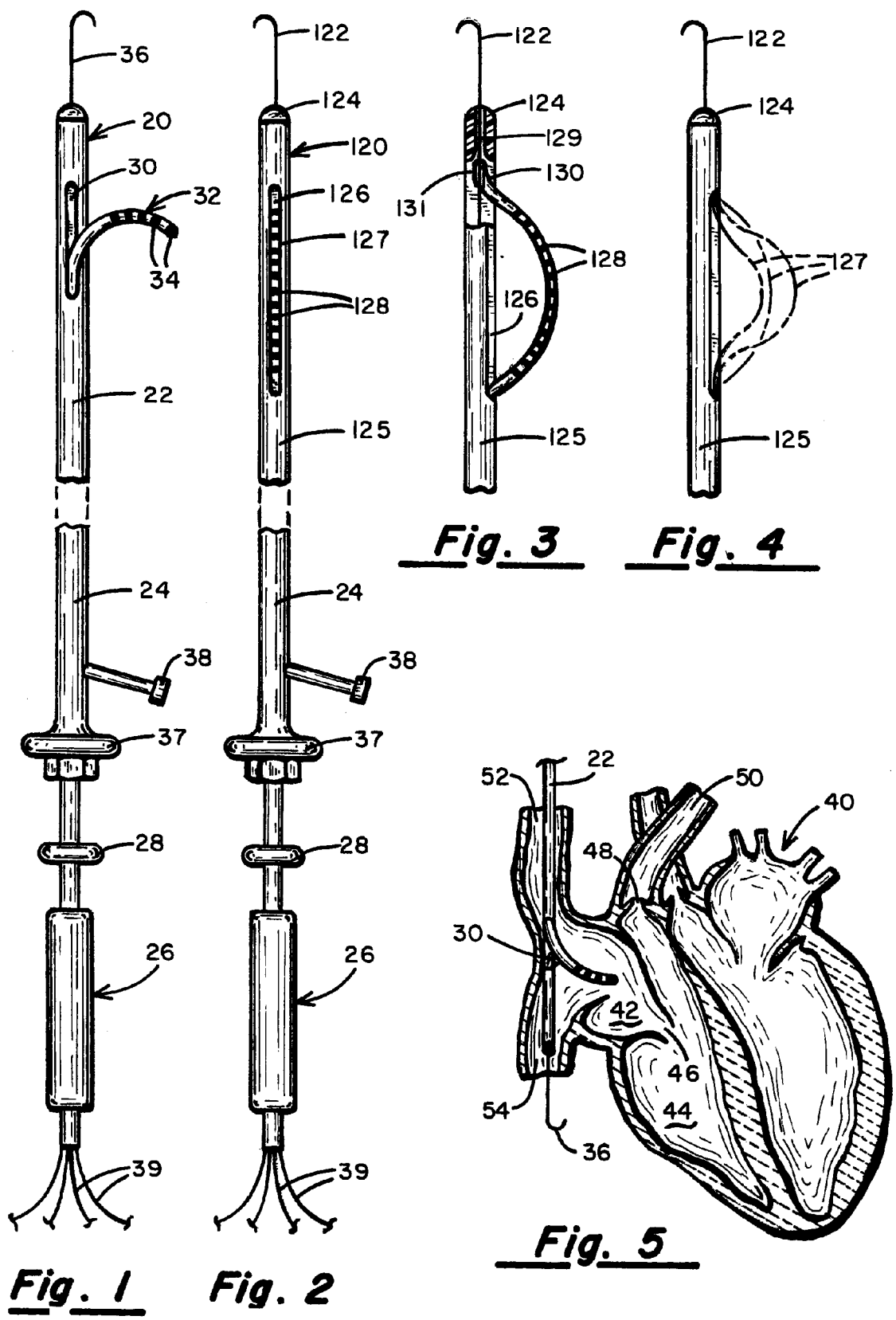

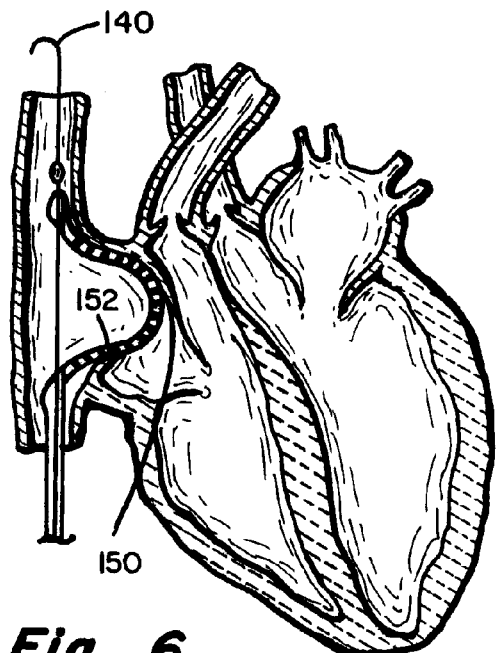
Fig. 6
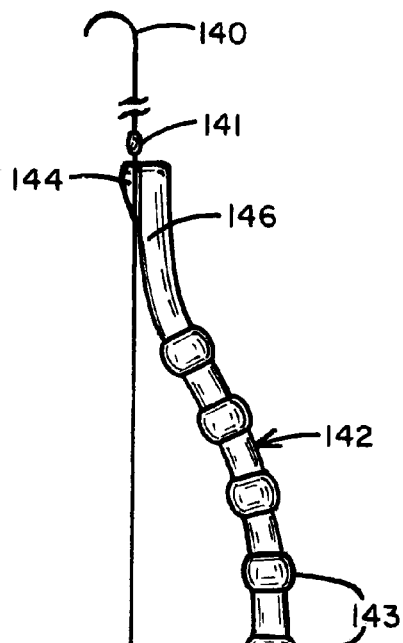
Fig. 8
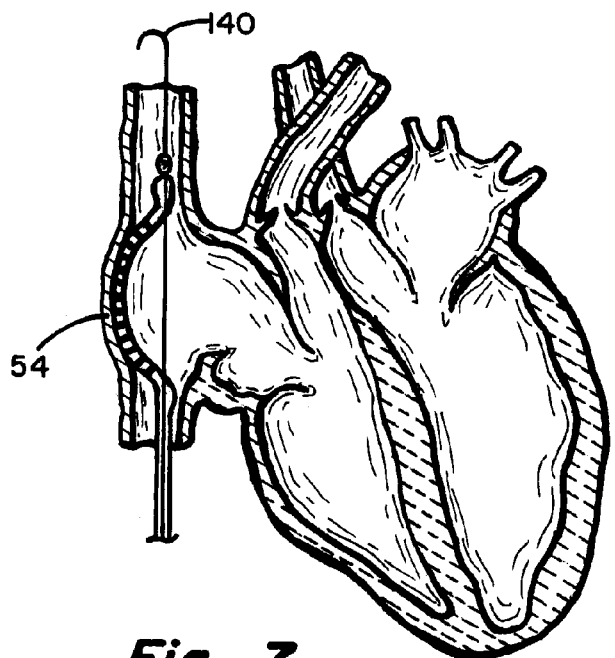
Fig. 7
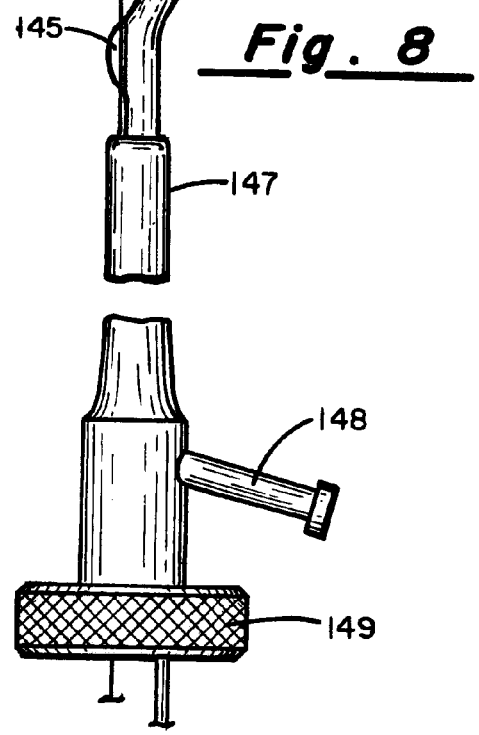

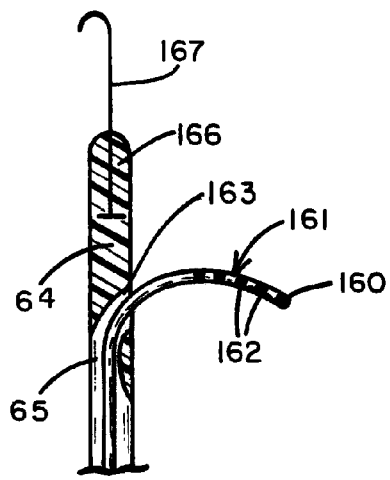
Fig. 9
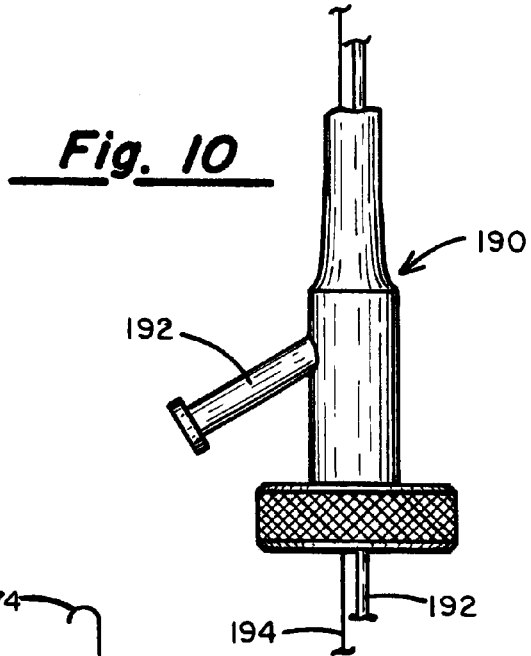
Fig. 10
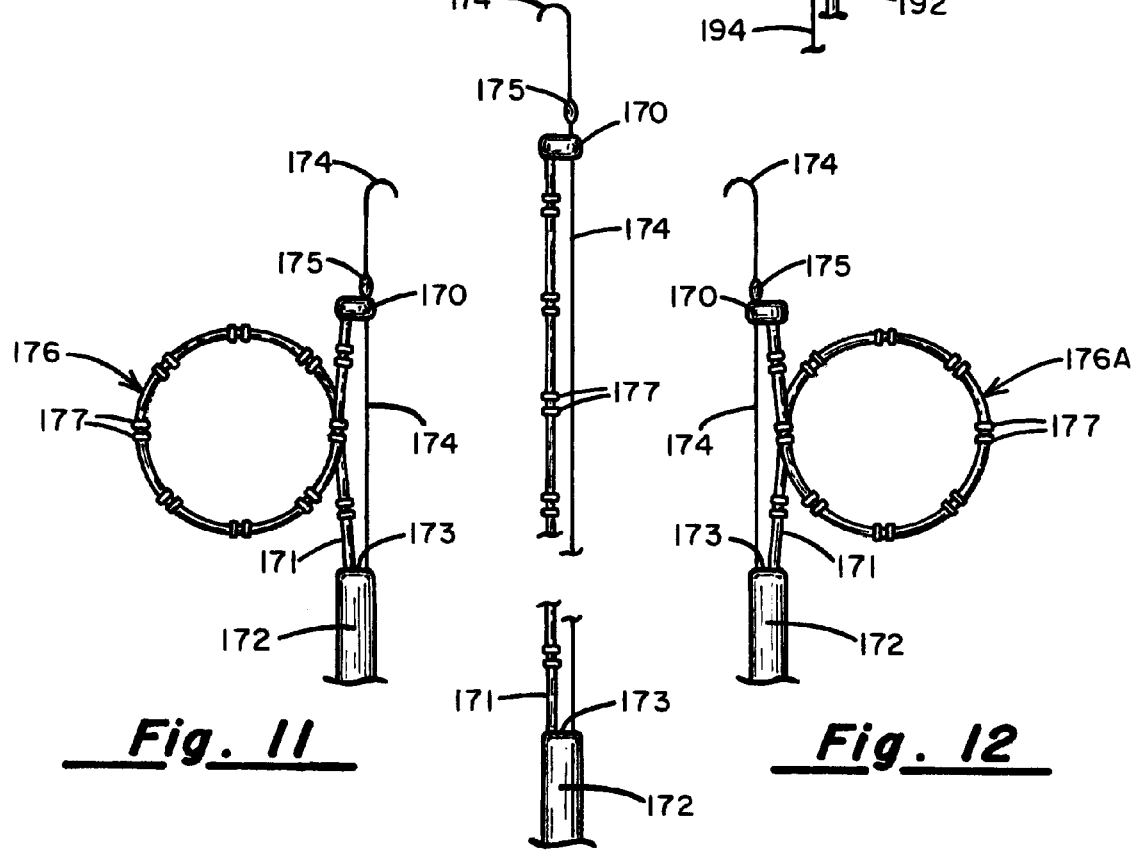
Fig. 11
Fig. 13
Fig. 12

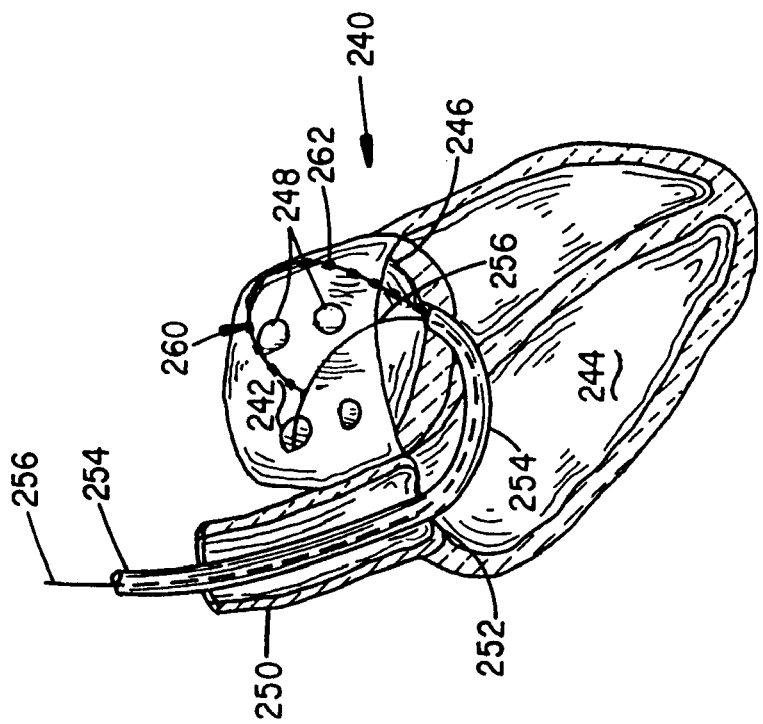
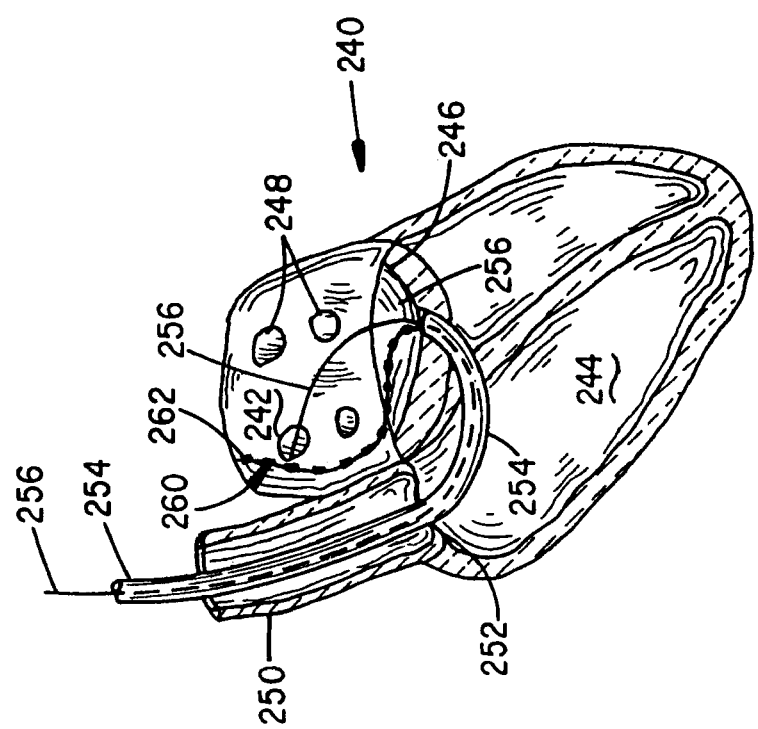
FIG. 17b
FIG. 17a

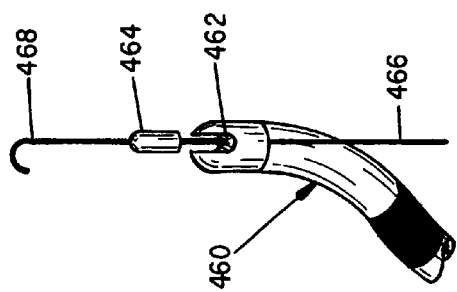
FIG. 32
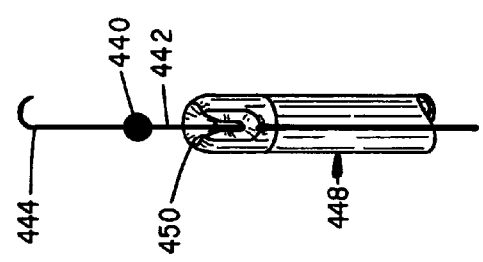
FIG. 31b
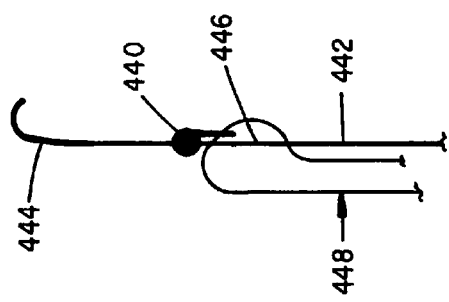
FIG. 31a
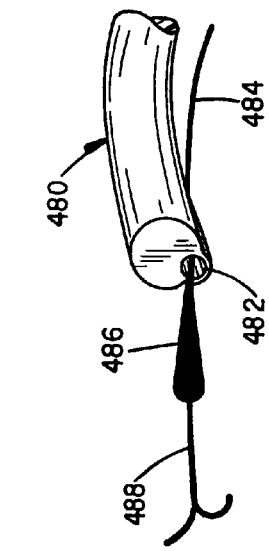
FIG. 34
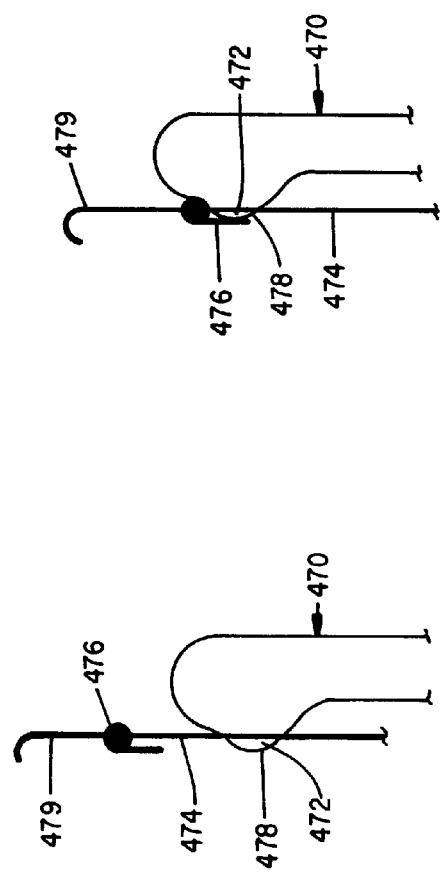
FIG. 33B
FIG. 33A

MAPPING AND ABLATION CATHETER SYSTEM

CROSS-REFERENCE TO RELATED APPLICATION

This application is a Continuation of application Ser. No. 09/154,854, filed Sep. 17, 1998 now U.S. Pat. No. 6,138,043 which, in turn, a Division of application Ser. No. 08/968, 159, now U.S. Pat. No. 5,842,984, filed Nov. 12, 1997, which was a Division of application Ser. No. 08/593,660, filed Jan. 29, 1996, now U.S. Pat. No. 5,730,127, which was a continuation-in-part of application Ser. No. 08/487,492, filed Jun. 8, 1995, now U.S. Pat. 5,687,723, which was a continuation-in-part of parent application Ser. No. 08/161, 920, filed Dec. 3, 1993, now U.S. Pat. No. 5,487,385.

BACKGROUND OF THE INVENTION

I. Field of the Invention

The present invention relates generally to the field of mapping and ablation using steerable vascular catheters. The invention is particularly directed to recording and ablation catheter systems applicable to create continuous linear lesions in any cardiac chamber.

II. Discussion of the Related Art

Steerable catheter systems of several types have been devised. Such devices can be inserted into blood vessels or similar bodily areas and their distal ends navigated through the tortuous vascular path to reach areas of the body normally inaccessible without surgery. Catheters of the steerable or self-navigating type, having distal electroded sections for monitoring parts of the body, such as for electrically mapping the heart by receiving and transmitting electrical signals related to the operation of that organ to recording signal processing and display devices are also known. The ability to successfully record impulses or signals and from them electrically map cardiac chambers and valves using flexible catheters having steerable electroded tips has further led to the development of techniques for transcatheter ablation of cardiac tissues that have been identified as the pathways that enable cardiac arrhythmias. This technique has emerged as one of the most important advances in cardiac electrophysiology. Its goal is to destroy the arrhythmogenic tissue without compromising the mechanical or muscular integrity of the cardiac tissues and vessels.

Not long ago, for example, many patients with Wolff-Parkinson-White syndrome or ventricular tachycardia were forced to undergo surgical dissection of the arrhythmogenic tissue followed by a painful and prolonged recovery. Introduction of the transcatheter approach has dramatically reduced the suffering and cost of definitive treatment for many cardiac arrhythmias.

The general approach to this procedure initially preferably utilized high energy direct current delivered to the catheter poles, for example, to disrupt the A-V node condition and even to create a complete heart block by ablating the His bundle. More recently, however, radio frequency has replaced high energy direct current as the preferred primary source of energy and the transcatheter approach for cardiac ablation has become an accepted and common procedure and has been used increasingly as the primary mode of treating cardiac arrhythmias. Transcatheter cardiac tissue ablation is more fully discussed in Avitall et al, "Physics and Engineering of Transcatheter Tissue Ablation", *JACC,* Volume 22, No. 3:921–32. The rapid clinical acceptance of this procedure and the proliferation of physicians engaged in transcatheter tissue ablation has mandated the development of improved steerable catheter devices.

Other common cardiac arrhythmias untreatable except with medication, and more recently, surgery, involve atrial fibrillation and flutter. These conditions, in fact, are the most common rhythm disturbances in human beings. For example, approximately 1% of the population of the United States, i.e., more than 2.5 million people, depends on medication to control this condition. These irregular heart rhythms can reach rates of 180 beats/minute or more. The resulting loss of blood flow due to incomplete atrial contractions along with a rapid heart rate can lead to shortness of breath, dizziness, limited physical endurance, chest pains, in patients with coronary heart disease, and other related problems.

Recently, Dr. Cox et al of Washington University School of Medicine in St. Louis, Mo., have devised a surgical procedure called the Maze and Corridor operation. This procedure is an attempt to restore the normal heart rhythm by segmenting the atrial tissues in a manner that allows the normal heart pacemaker to conduct to the AV node as well as preventing the atrial tissues from sustaining the atrial fibrillation. By cutting the atrial tissue, no electrical activity can be transmitted from one segment to another, thus making the segments too small to be able to sustain the fibrillatory process. The approach, while successful, has the same drawbacks as other previous surgical approaches with respect to the recovery of the patient. This represents another area of cardiac arrhythmic treatment where a more benign approach, i.e., without invasive surgery, would represent a definite advance.

In this regard, as with certain other arrhythmia conditions, electrical decoupling of tissues by heating the tissues with radio frequency (RF) energy, microwave energy, laser energy, freezing and sonication, represent possible alternative approaches. Heating tissues above 55° C. is known to cause permanent cellular injury, making the cells electrically silent. It has been found that segmenting tissues by creating continuous linear lesions via ablation in the atria mimics some aspects of the maze and corridor procedure. The most important aspect of these lesions is their transmural and continuous character; otherwise, segmenting the heart and preventing atrial fibrillation would not be possible. However, it is possible that limited division of tissues within the right atrium may prevent atrial fibrillation in some patients. Furthermore, segmenting a corridor between the sinus node and the AV node will maintain physiological control of heart rate despite the fibrillation of the atrial tissues.

Present steerable catheter systems, while successful in addressing many internal cardiac areas, have not been so successful in treating atrial fibrillation, for example, because they have not been able to sustain contact with certain surface areas of the atrial chambers without great difficulty. In this regard, prior devices have failed to successfully create the necessary linear lesions via ablation to achieve the desired segmentation. The provision of a recording and ablation catheter system that can successfully treat atrial fibrillation and flutter and other conditions as by making creation of continuous linear lesions in the relevant chamber easier would represent a definite advance in the treatment of this condition.

Accordingly, it is a primary object of the invention to provide an improved catheter, easily deployed and maneuvered to contact desired inner wall surfaces of the any cardiac chamber and sustain contact so that linear lesions can be produced as required.

Another object is to provide multi-electrode working catheter shapes that are easily deployed from sheaths or main catheters once the desired chamber is reached.

An additional object of the invention is to provide such catheter shapes capable of being readily modified to address internal surfaces of varying contour in a linear manner.

Yet another object of the invention is to provide a method of readily mapping and ablating in an atrial chamber.

Still another object of the invention is to provide an improved multi-electrode mapping and ablation catheter for deployment in an atrial chamber by accessing one atrial chamber from the other atrial chamber through the atrial septum.

Yet still another object of the invention is to provide an improved multi-electrode mapping and ablation catheter for deployment in the left atrial chamber that accesses the left atrial chamber via the inferior or superior vena cava, right atrial chamber and the atrial septum.

A further object of the invention is to provide an improved multi-electrode mapping and ablation catheter for deployment in the left atrial chamber capable of aligning multiple electrodes in any disposition with reference to the wall of that chamber.

A still further object of the invention is to provide a multi-electrode mapping or ablation catheter for deployment in an atrial chamber by accessing the atrial chamber via the aorta.

A yet still further object of the invention is to provide a multi-electrode mapping or ablation catheter for deployment in the left atrial chamber by accessing the left atrial chamber via the aorta and that is capable of ablating a linear lesion of any disposition within the left atrial chamber.

An additional object of the invention is to provide a multi-electrode mapping and ablation catheter deployable in a heart chamber having a plurality of shape controlling devices associated with the deployed system.

Yet an additional object of the invention is to provide a multi-electrode ablation catheter with integral electrode cooling.

Another object of the invention is to provide a deployable mapping and ablation catheter for creating linear lesions in the form of a deployable ribbon loop device.

Yet another object of the invention is to provide an over the wire and a fixed wire multi-electrode mapping and ablation device with relative rotation control.

Other objects and advantages of the invention will become apparent to those skilled in the art in accordance with the descriptions and Figures of this specification.

SUMMARY OF THE INVENTION

By means of the present invention, there is provided an array of readily controlled arcuate distal working catheter shapes that form the distal portion of an inner catheter carried by an outer catheter or sheath. The catheters may also be in the form of ribbon like structure which can be displayed from a sheath to form symmetric or asymmetric loop configurations. The working catheter sections are easily deployed to contact the inner wall surface of any cardiac chamber in a manner that allows them to contour the endocardial surface and enables easy recording or mapping of impulses and thereafter facilitates sustained contact so that linear lesions can be produced from an array of mapping and ablation electrode devices serially spaced along the working catheter shape using the electric heating or radio frequency ablation energy.

The inner catheter is provided with a distal electroded section known as the working catheter section and is inserted through or carried within a lumen of a main vascular catheter or sheath and the working catheter section of the inner catheter is designed to be deployed from the main catheter or sheath once the desired chamber is entered. The main catheter or sheath is provided with an opening at or near the distal end from which the distal portion of the inner catheter or working catheter section is caused to emerge. Using any of several posturing techniques, the working catheter section may be caused to assume any of several deployed shapes, the control of which may be independent of or with reference to the slidable attachment of one or both ends of the working catheter section to an axially displaceable guidewire or other catheter mounted element.

While certain configurations may favor one or the other, it is contemplated that the working catheter of the invention be deployable and fully effective in any heart chamber including either atrial chamber. It is further contemplated that the working catheter section or electroded distal section be one which can access either atrial or ventricular chamber and embodiments are provided for using more than one access route. In this manner, the left atrial chamber, for example, may be accessed via the arterial system through the aorta, the left ventricle and the mitral valve; or through the venous system through either vena cava (the use of the inferior vena cava is illustrated in the Figures) and thereafter piercing the atrial septum to access the left atrial chamber. Once the chamber of interest has been entered in the manner desired, the electroded portion or section which may conveniently be called the working catheter section may be deployed and maneuvered into the desired pattern of contact with the chamber wall. Both mapping and ablation procedures may be combined or achieved singularly using the special deployment and electrode configurations of the invention.

It is important that control of the disposition or posture of the working catheter within the chamber to be treated be made as easy as possible so that the desired alignment at the ablation site can be achieved in the shortest time. Another important aspect of the invention is that the working catheter be able to be controlled so as to sustain an electrode position until ablation is accomplished.

Positioning may also be assisted in certain embodiments by providing additional control devices. In catheters designed to operate slidably over a guidewire, a locking system may be provided in any of several forms to optionally prevent rotation of the distal portion of the catheter relative to the guidewire. In other self-guiding embodiments, the distal end may be permanently fixed to a control wire.

If desired, the ablation catheter may be provided with an auxiliary cooling system to prevent overheating of the tissue adjacent or abutting ablation electrodes after they have been energized. This system flushes desired electrodes with infused saline from an encased movable internal tube through cooling effusion ports provided tube which can be aligned with pores or ports provided in the working catheter and in the electrodes themselves which can be connected with a source of fluid coolant.

The working catheter of the invention may be deployed independently of or may include one or more rider devices which slidably thread over a wire member, which may be the guidewire, and which cooperate with stops limiting travel of at least one of the rider members such that adjustable arcuate forms are assumed by the section intermediate the rider members as their relative separation distance is modulated. A linear or non-linear semi-rigid tube guide member may also be used in conjunction with the guidewire in posturing the working catheter. Additional control elements may be attached along the working catheter between electrodes to provide additional shape modification. In another alternate embodiment, a right- or left-handed loop shape is assumed by the specialty shaped working catheter upon deployment. One or more radiopaque markers may also be provided to assist in positioning and orienting the system.

BRIEF DESCRIPTION OF THE DRAWINGS

In the drawings, wherein like numerals designate like parts throughout the same:

FIG. 1 is a schematic representation of one embodiment of an atrial fibrillation mapping and ablation catheter in accordance with the invention with the extended length of the main tube segment broken away;

FIGS. 2–4 illustrate a different embodiment of a mapping and ablation catheter;

FIG. 5 illustrates schematically the deployment of the catheter embodiment of FIG. 1 in a right atrial chamber;

FIGS. 6 and 7 depict the deployment of the embodiment of FIG. 8 in a right atrial chamber;

FIG. 8 is an enlarged schematic representation of an alternate to the embodiment of FIGS. 2–4 of a working catheter in accordance with the invention with the elongated sheath shown broken;

FIG. 9 is a schematic representation of yet a different embodiment of the catheter of the invention;

FIG. 10 is an enlarged fragmentary view illustrating an infusion port usable with the catheter system of the invention;

FIGS. 11–13 are fragmentary views of yet a different embodiment of the catheter of the invention which takes the form of a loop configuration when deployed;

FIGS. 17a–17d are additional views similar to FIG. 16 showing the working catheter section of the invention accessing a variety of surfaces in the left atrial chamber accessed by the route of FIG. 16;

FIGS. 31a and 31b depict fragmentary front and profile views of one version of a rotation control lock for a guidewire mounted catheter tip;

FIGS. 32, 33a, 33b and 34 depict additional embodiments of guidewire mounted catheter tip rotation control lock mechanism;

DETAILED DESCRIPTION

Figure 15A:
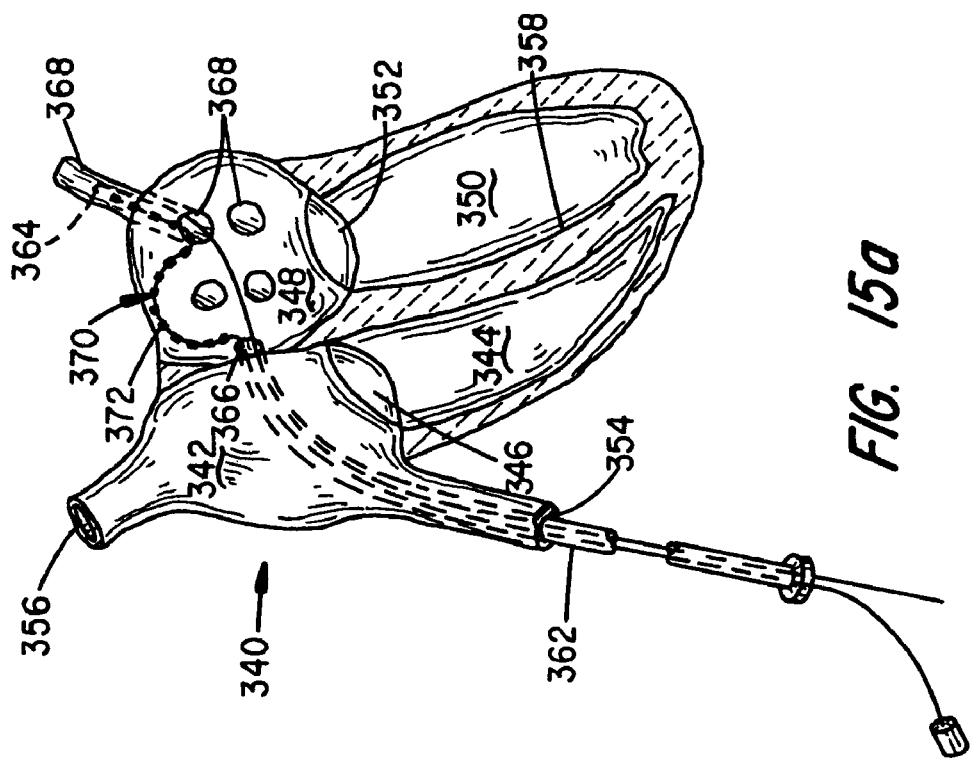
FIGS. 15a–15d are additional views similar to FIG. 14 further illustrating the accessibility of a variety of areas of the surface of the left atrium accessed as per FIG. 14 and using the working catheter section of the invention.

The electrical mapping and ablation system is carried by a distal working catheter or probe portion, extension or segment which, in accordance with the invention, may present itself in any of several forms. The distal portion or area is normally deployed from a main catheter or sheath in the vicinity of any cardiac chamber of interest. The electrode position and form chosen will depend on the particular surface to be addressed and the mode of access to the chamber. Also, the electrode configuration is not meant to be limited in any manner to the illustrated patterns, it being further understood that any size and pattern of electrodes consistent with mapping and ablation objectives in any part of the chamber of interest can be employed.

The electrode systems in accordance with the distal working catheter section are generally designed so that each individual electrode is electrically connected by a separate insulated lead threaded through the catheter system to the distal end thereof where each lead is connected to a control system that enables separate mapping or recording of impulses received from each electrode and separate or ganged connection of the same electrodes for ablation. This enables ablation using any desired pattern of multiple electrodes in the serial array to produce any configuration of desired lesions. Such an arrangement of electrode control is illustrated and described in applicant's co-pending application Ser. No. 08/161,916 filed of even date with the grandparent of this application (Dec. 3, 1993) and now U.S. Pat. No. 5,454,370 issued Oct. 3, 1995, which is hereby incorporated by reference for any necessary purpose.

The working catheter of the invention is designed to enable the skilled practitioner to achieve a greater degree of control with respect to mapping and precisely placing linear lesions in the internal surface of tissue in the vicinity of a cardiac chamber with greater facility using RF ablation or the like to achieve electrical segmentation. This is achieved by the provision of a variety of unique working catheter embodiments configured to contact continuous segments of atrial chamber surfaces. While certain of the embodiments may be described with particular reference to a specific cardiac chamber, it will be understood that the working catheters of the invention may find further equally viable use in other chambers and organs. Thus, for example, the various embodiments described with relation to atrial ablation may also be used in ventricle chambers and also in the vicinity of heart valves as well.

Such a catheter, shown generally at 20 in FIG. 1, includes three main cooperating components including a distal working catheter sheath section or portion 22, which may be an extension of an elongated main tubular catheter member 24 shown broken to indicate the relatively extensive length, and a control handle 26 with a working tip manipulation or orientation control knob as at 28. The working catheter sheath section is provided with a slotted opening 30 from which a flexible segment or relatively short distal length of working catheter 32 which can readily be deflected or bent and which carries a plurality of serially spaced electrodes as at 34 emerges to be deployed. The control knob 28 may be attached to deploy and spatially manipulate (deflect and rotate) the working catheter section 32 in any well-known manner. One such control system is illustrated and described in the applicant's copending application Ser. No. 08/156,284 filed Nov. 22, 1993, now U.S. Pat. No. 5,465,716 issued Nov. 14, 1995, entitled Catheter Control Handle. Material from that application to the extent helpful or necessary to this description is further deemed incorporated herein by reference for any necessary purpose. In any event, the working catheter portion 32 is deployed from the sheath opening 30 and is designed to be manipulated both as to curvature and posture to position the electrodes against a surface to be mapped or ablated.

The catheter 20 further includes a short relatively flexible vascular guide member 36 fixed to the distal tip thereof to enable the device to be essentially self-navigating. A liquid-tight sheath locking device 37 with infusion port 38 is provided proximal the point of catheter introduction which cooperates with an introducer device in a well-known manner such that catheter controls and input/output devices are accessible from outside or proximal the point of catheter introduction. A plurality of conductors are shown at 39.

FIG. 5 is a schematic representation of a heart 40 sectioned through the chambers including a right atrial chamber 42, right ventricle 44, separated by tricuspid valve 46. The pulmonary valve and artery are shown, respectively, at 48 and 50. The superior vena cava is shown at 52 and the inferior vena cava, at 54. The working catheter section is shown in the right atrium and extending in the vena cava and illustrates that the right atrial chamber 42 can be accessed either through the superior vena cava or the inferior vena cava and the electroded working segment deployed in conjunction with movement of the sheath 22 to enable placement of the electrodes 34 as desired.

FIGS. 2–4 depict an alternative functional embodiment 120 of the catheter/sheath of the invention in which the guidewire or guide tip 122 protrudes from a closed distal end 124. The sheath section or portion 125 is provided with an elongated slot or opening 126 through which the working catheter section 127 with a plurality of electrodes 128 is deployed. As better seen in FIG. 3, in this embodiment the guide member 122 extends into the lumen 129 of the sheath 125 and is further slidably threaded through a bore 130 in a rider segment 131 in the distal end of the working catheter section 127.

The working catheter section 127 has the rider of its distal end slidably threaded over the vascular guide member that the more proximal portion of the catheter section 127 produces an adjustable arcuate curve in the electroded working catheter section. A control wire attached in the proximal area of the distal working catheter section in a well-known manner as, for example, described in the above cross-referenced copending applications, when reciprocally manipulated as by handle 28 will produce an arcuate curve of varying severity as illustrated in FIGS. 3 and 4. In this manner, the plurality of serially spaced electrodes 128 can be caused to assume an adjustable pattern that can be placed adjacent chamber surfaces of varying arcuate shapes; FIG. 4 illustrates a plurality of possible configurations. The nose portion 124 provides a distal stop that determines the furthest distal location of the tip rider 131 of the distal catheter segment 126 so that further distal directed longitudinal displacement of the proximal portion of the working catheter within the sheath will produce arcuate deflections to form configurations such as those illustrated.

FIG. 8 is an enlarged schematic view of a guidemounted embodiment using a slideover-type flexible guiding, navigation member or wire 140 over which the working catheter section 142 with electrodes 143 is threaded both distal and proximal the electroded portion using rider segments as illustrated at 144 and 145, respectively, leaving the central portion detached to form a "caterpillar" attachment arrangement. A positive stop 141 attached to the guide member 140 limits the distal travel of the catheter tip. The main catheter sheath is shown at 147, broken away for convenience, and optionally provided with an infusion port 148 with lock system 149.

The number, size and spacing of the electrodes 143 is optional. One embodiment used 20 ring electrodes about 4 mm long, spaced 4 mm apart. It will be appreciated, however, that the serially spaced electrode configuration in accordance with the invention and its several embodiments has as a primary goal, aside from arcuate tissue mapping or recording, the creation of linear lesions by means of ablation to achieve segmentation of conduction paths within the chamber surface tissue. With this in mind, certain combinations of electrode configurations and shapes can be employed. Electrodes~2 mm in length spaced 0.5–3 mm apart in the embodiments of FIGS. 1–4 and 9 have also been used as have electrodes arranged in spaced pairs as in FIGS. 11–13.

The embodiment of FIG. 8 is further illustrated with respect to catheter placement in the right atrial chamber of a heart in FIGS. 6 and 7. These schematic sectional views illustrate that the relative arcuate shape of the mapping/ablation working catheter section 142 can be controlled to any desired shape and that such arcuate shapes very closely resemble the contour shapes of the internal surfaces of the various walls of the right atrium. In FIG. 6, for example, the upper interior section 150 is readily addressed by the arcuate shape assumed by the working catheter section 142 as is the lower segment 152. In FIG. 7, the right wall of the atrial chamber is addressed at 154. The working catheter section has further been rotated with respect to the guide member 140. These positions can be maintained despite continuously flowing blood and moving chamber walls.

With respect to the embodiment of FIG. 8, a 7F sliding catheter system similar to that of FIG. 8 was constructed that allowed the catheter to curve and adapt to the endocardial surface of the right atrium. The catheter was equipped with 20 closely spaced 4 mm electrodes used for both mapping and ablation. In 7 models, susceptibility to AFIB was created by sterile pericarditis, vagal stimulation and isuprel infusion (3 μgram/min). A stiff guidewire with a floppy pigtail tip (as at 140 in FIG. 8) was inserted via the femoral vein into the superior vena cava. A sheath was placed over the guidewire with its tip at the inferior vena cava/right atrial junction. The ablation catheter was inserted into the sheath over the guidewire and initially positioned at the posterolateral right atrium with the electrodes in contact with the superior vena cava, right atrium and inferior vena cava tissues. Catheter deflection was achieved by pushing the catheter shaft against a stopper located 10 cm from the guidewire tip.

Graded RF power starting at 20 watts and proceeding to 30, 40 and 50 watts was applied to each electrode for 30 seconds at each power level. Following the ablation, the catheter was moved and curved over the anterior wall of the right atrium and the ablations were repeated. AFIB was induced at least 10 consecutive times before and after ablation using 60 Hz alternating current applied for 5 seconds to the left atrial appendage. Six of the 7 models had sustained AFIB (>3 min). Following the ablation, AFIB could not be sustained and lasted only 20±48 seconds. Examination of each heart revealed continuous transmural lesions bisecting the right atrium posterolaterally and anteriorly.

FIG. 9 illustrates yet another embodiment in which the distal end or tip 160 of the working catheter segment 161 with electrodes 162 is deployed from a guided distal opening 163 in the distal end of a lumen 165 in a catheter or sheath 166 equipped with a flexible soft wire tip-type vascular guide member 167. In this embodiment, as with the embodiment of FIG. 1, the amount of deployment, deflection and posture of the working catheter tip section 160 may be controlled by handle manipulations means in conjunction with one or more control wires or elements (not shown).

FIGS. 11–13 depict yet another configuration for providing an arcuate shape suitable for mapping and ablation within the confines of the right atrial or any other desired chamber of the heart. As can be seen in those Figures, the distal end 170 of a distal working catheter section 171 emanating from a sheath or main catheter 172 at 173 has a bore slidably threaded through a flexible guidewire 174 provided with a positive stop member 175 fixed a predetermined distance from the distal navigating tip end of the guidewire 174. A control wire (not shown) attached through the working catheter 172 is used to axially adjust the position of the proximal end of the working catheter section 172 in relation to the stop to thereby form and adjust the relative size of the essentially circular loop 176. In this manner, the loop 176, 176A may be made larger or smaller in a given set amount thereby enabling it to address right atrial chambers of different sizes and be expanded against arcuate shapes of varying radii. It can also assume a substantially linear shape prior to or after deployment to be retracted into the catheter or sheath. Whereas the electrodes 177 are depicted in spaced pairs, other configurations such as that of FIG. 8 can be used.

FIGS. 11 and 12 depict opposite-handed circular loops which can be formed from the working catheter shown broken in FIG. 13. The device may be predisposed to form a right- or left-handed loop with regard to a given orientation of the catheter and depending on the direction of entry into the right atrium or other chamber and/or the particular surface to be mapped and/or ablated, one or the other might be preferable. Otherwise, the two are the same.

With respect to the dimensions of the various embodiments of the catheters of the invention, the working catheter segments are typically about 5 French to 8 French in diameter and the sheath member is approximately 7–10 French in diameter. The catheters having sheath or side openings, typically extend approximately 5 mm beyond the openings 30, 126, etc. and approximately 15 cm beyond the opening in the embodiment of FIG. 9. The working catheter segments are typically 5–15 cm in length in the case of the segments 127, 146 and somewhat shorter in the case of segments 32 and 160. The loop configurations of FIGS. 11 and 12 may be any desired length but typically are such that the loop approximates the size of the caterpillar design of FIGS. 3, 4 and 8.

FIG. 10 illustrates an alternate infusion system to that of FIG. 8, or the like, and includes an infusion port 192 above a catheter or sheath seal and lock (not shown) and the electrode conducting wires as at 192 and possibly a guidewire and/or control member 194 can be provided with passage through the system to the proximal controls.

Figure 14:
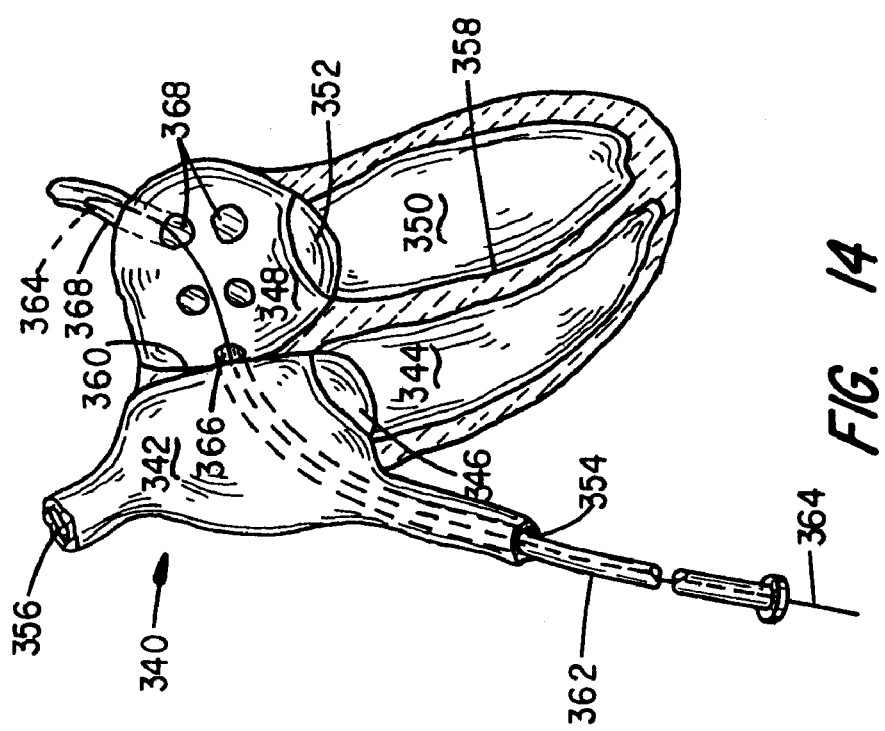
FIG. 14 is a simplified schematic front diagram partially in section of a heart illustrating the chambers and an accessing route to the left atrial chamber through the inferior vena cava and atrial septum.

FIG. 14 is a simplified schematic frontal diagram of a heart 140 including a right atrial chamber 142 and right ventricle 144 separated by tricuspid valve 146. The left atrial chamber is shown at 148 and left ventricle at 150 separated by mitral valve 152. The inferior vena cava is shown at 154 and the superior vena cava at 156. The ventricular septum is illustrated by 158 and the atrial septum is shown at 160. A catheter sheath is shown at 162 with guidewire 164 extending through the inferior vena cava, and through the right atrium and just penetrating the left atrium at 166. The guidewire 164 is further shown extending into one of the left pulmonary veins 168 which connect and lead into the left atrium.

FIG. 15a is similar to the schematic diagram of FIG. 14 depicting a guidewire mounted distal working catheter section 170 having a plurality of spaced electrodes 172 deployed in a generally arcuate shape to contact a segment of the surface of the upper section of the left atrium. FIG. 15b is similar to FIG. 15a with the electroded catheter segment 170 deployed in a different contour contacting a lower surface of the left atrium, possibly in the vicinity of a cusp of the mitral valve 152. Of course, by advancing or anchoring the distal end of the guidewire in a pulmonary vein, as at 168, adjustment of the electroded segment is facilitated.

Figure 15C:
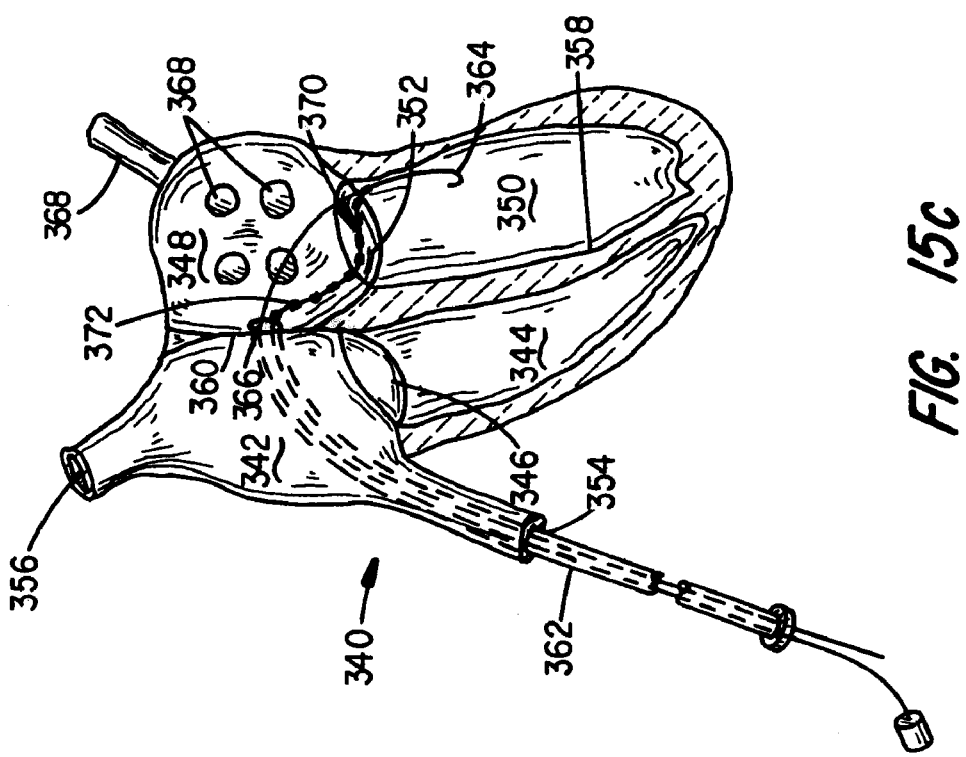
Figure 15B:
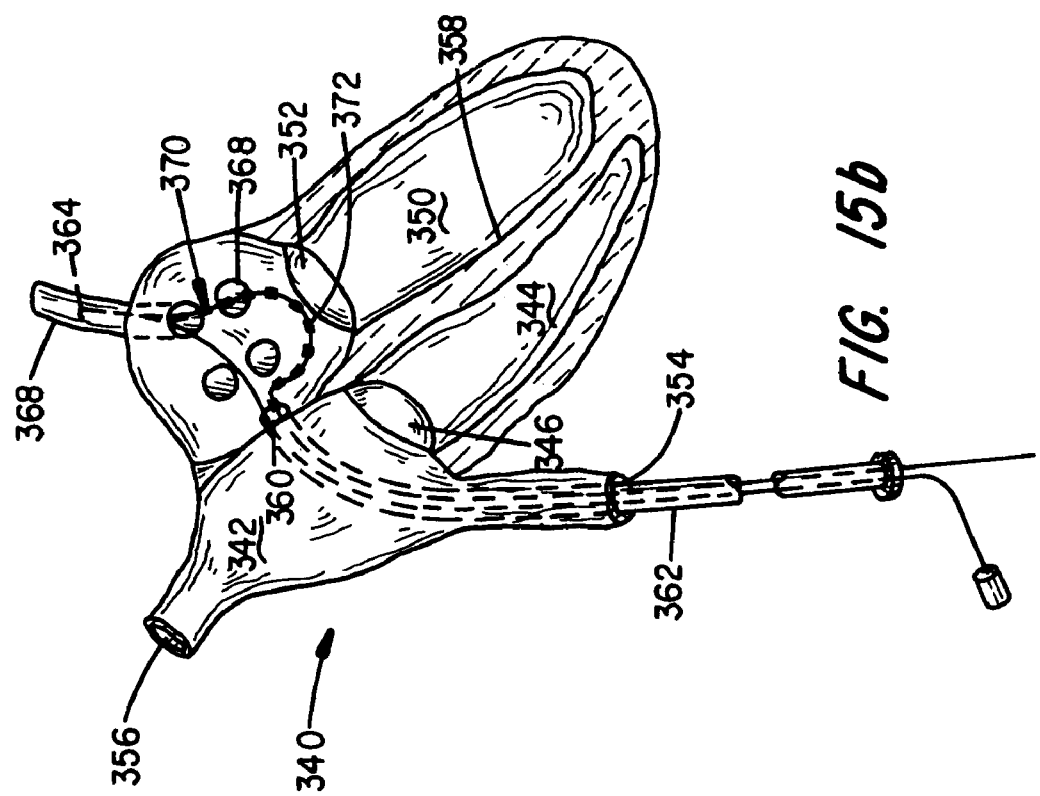
Figure 15D:
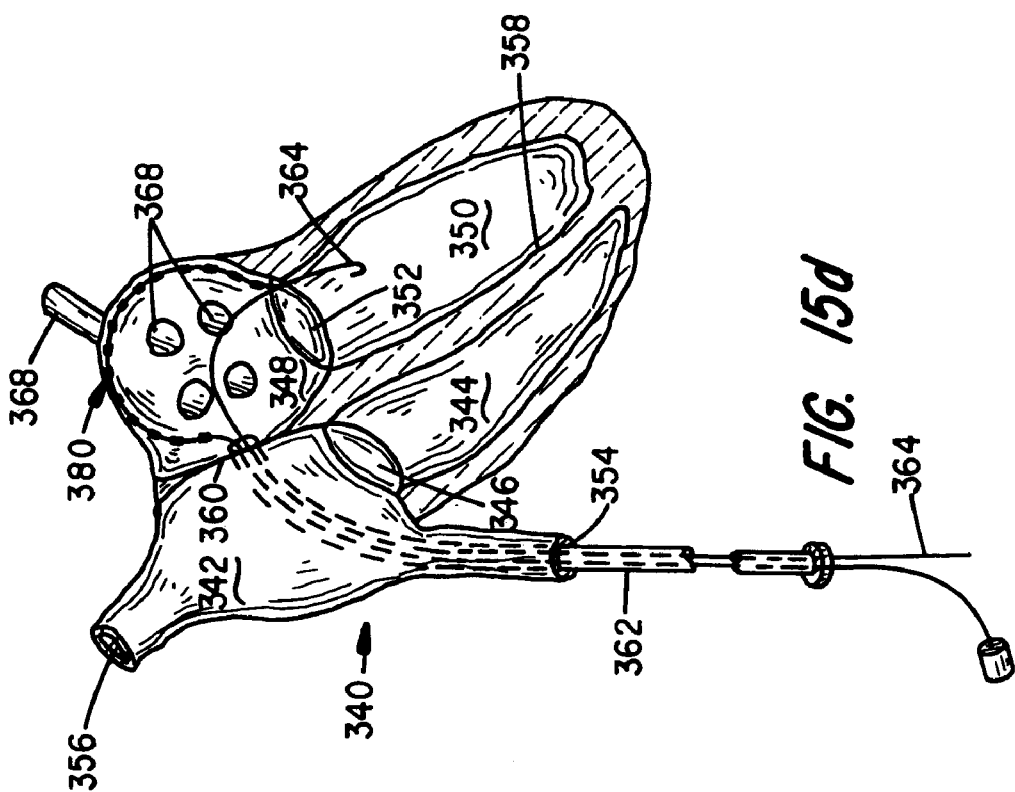

In FIG. 15c, the guidewire 164 is shown as extending through the mitral valve 150 into the left ventricle chamber 150 to leverage the deployment of the working catheter section 170 against yet a different atrial wall area. FIG. 15d depicts the use of an elongated or more fully deployed working catheter section 180 to contact a longer linear segment of the wall of the left atrium.

Figure 16:
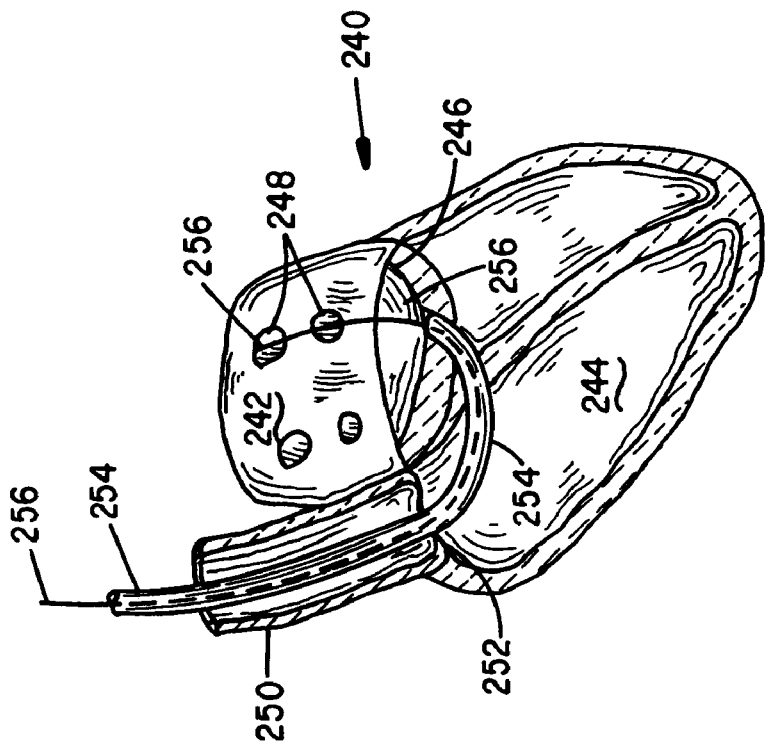
FIG. 16 is a simplified schematic front sectional diagram partially in section of a heart showing an alternate access route to the left atrium through the arterial system.

FIG. 16 illustrates an alternate way to effectively employ the electroded catheters of the invention to map and/or ablate in the left atrium. It includes a partial schematic diagram of a heart 240 with left atrium 242, left ventricle 244, mitral valve orifice 246 with pulmonary veins as at 248. A portion of the aortic arch is shown at 250 with aortic valve 252. A guiding deflection control sheath 254 with distally protruding guidewire 256 is seen entering the left atrium via mitral valve 246 and the extending guidewire is again extended into a left pulmonary vein 248.

Figure 17D:
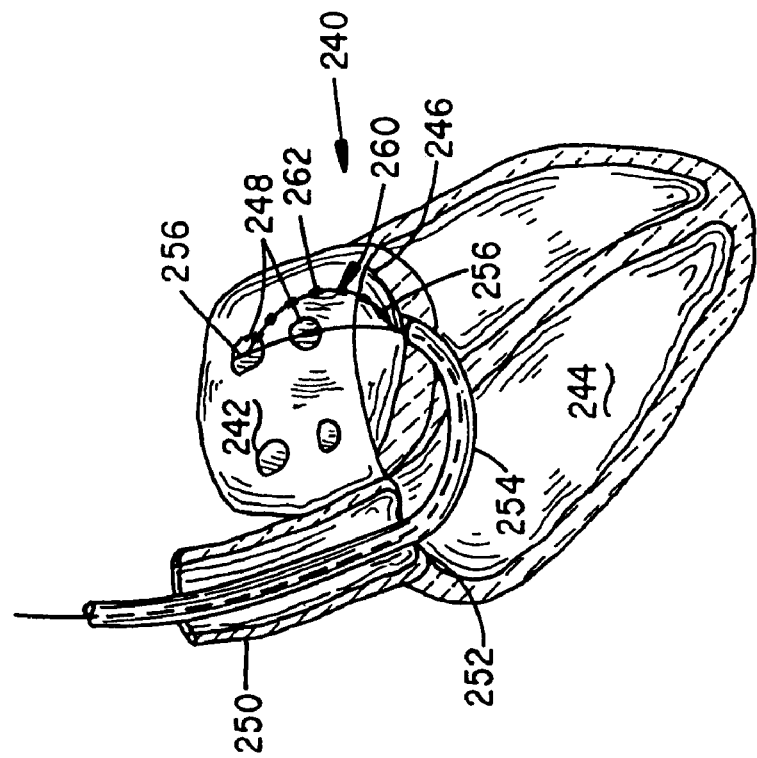
Figure 17C:
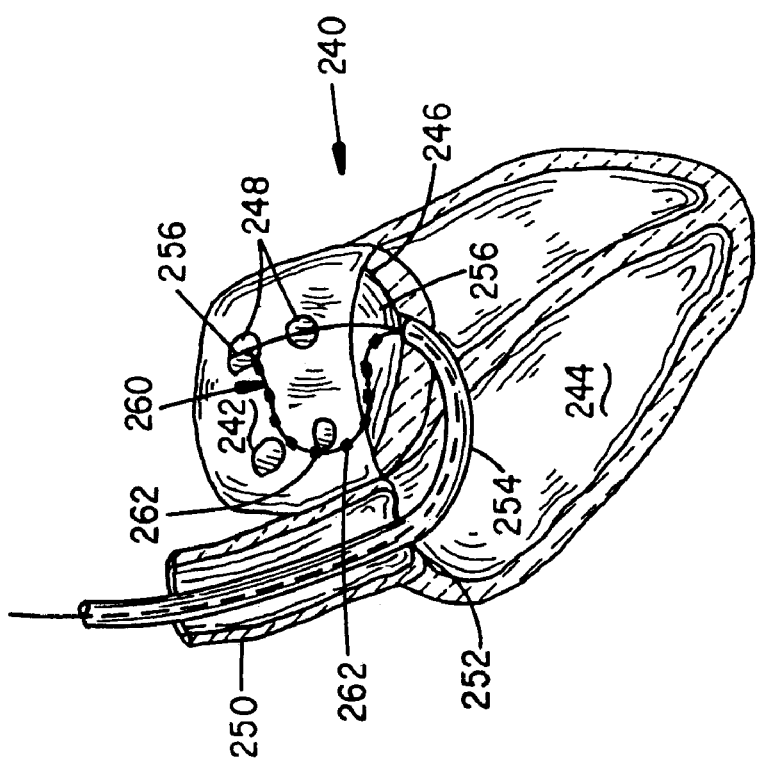

FIGS. 17a–17d are similar to FIGS. 15a–15d in that they portray the deployment of electroded working catheter segments 260 with electrodes 262 within the left atrium in a variety of dispositions to illustrate the extremely versatile nature of the catheter embodiment of the invention. The guidewire may be inserted into a right pulmonary vein as at 249 in some applications as shown in FIGS. 17a and 17b. The deployments of the FIGS. 14–17 may be accomplished by any of the catheter embodiments using a distal guidewire rider as in the embodiments of FIGS. 2–4 and 11–13; or distal and proximal guidewire riders as in FIG. 8. As illustrated, any amount of electroded working catheter length necessary can be employed and linear lesions of any length desired can be created.

Figure 18A:
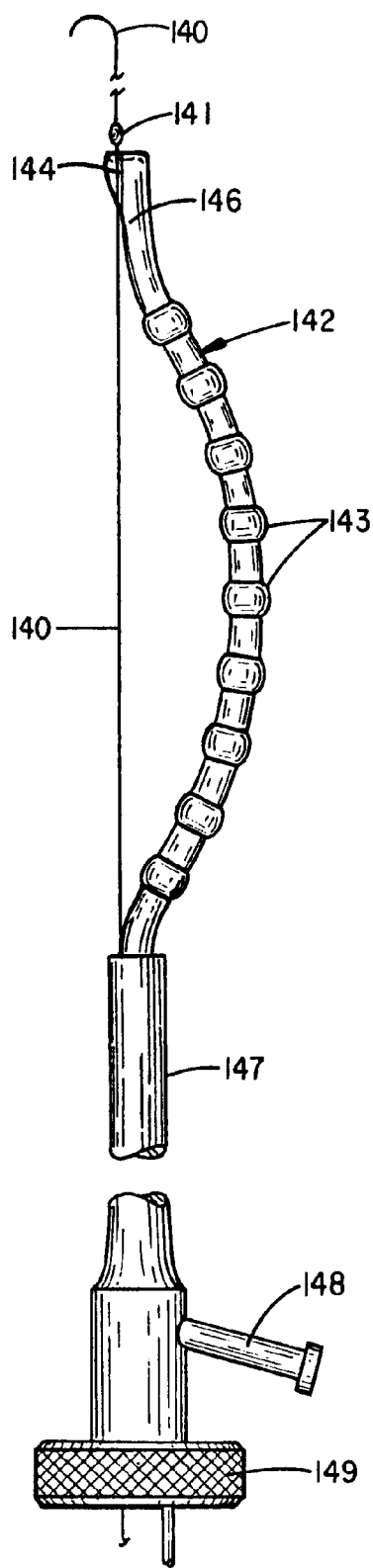
FIG. 18a is a view similar to FIG. 8 slightly reduced and with a single (distal) guidewire port.

FIG. 18a further depicts a catheter generally similar to that of FIG. 8 but which is provided with a single distal guidewire rider or eye 144 which rides on the guidewire 140. The proximal end of the working catheter 142 is retained by the sheath 141 independent of the guidewire 140. The guidewire steering distal floppy hook device is optional and may be removed leaving only a positive stop illustrated by stopper ball 141 at the distal extreme of the guidewire. Movement of the guidewire relative to the working catheter section 142 is used to provide at least part of the arcuate shaping of the working catheter to address the wall of a chamber of interest once that chamber is penetrated.

Figure 18B:
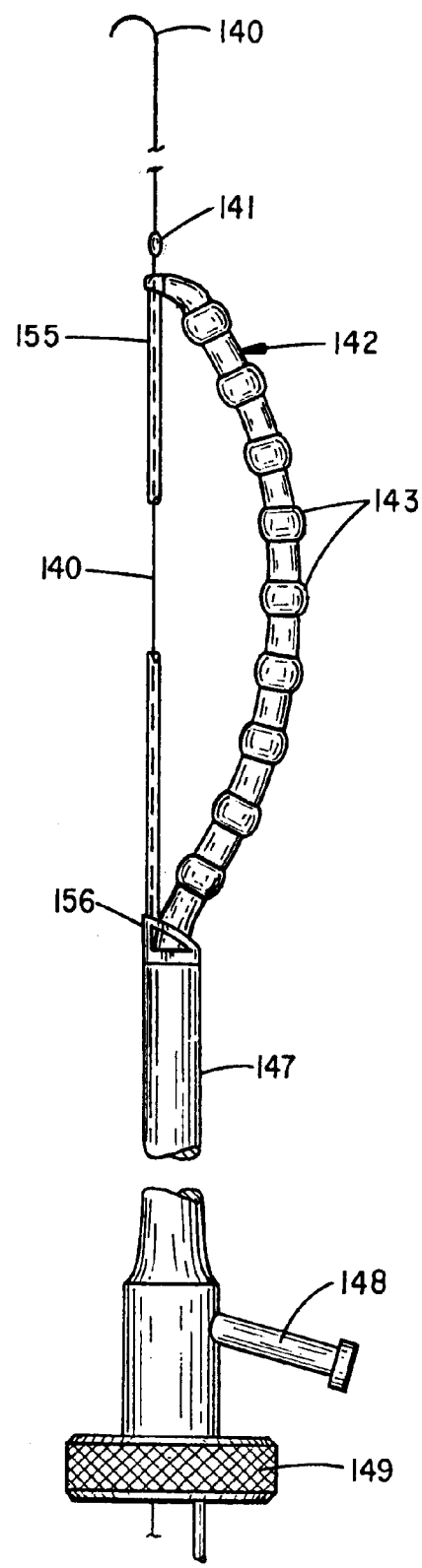
FIG. 18b is a view similar to FIG. 18a depicting a semi-rigid tubular control member.

FIG. 18b shows yet a different control approach in which a semi-rigid metallic or other type tubular member 155 is threaded over the guidewire 140 to stabilize the shape of the working catheter section 142. A radiopaque, preferably metallic, ring member 157 is shown which can be used to reference the location of the distal end of the sheath 147. The shape of the radiopaque member 157 is also such that the directional orientation of the sheath member 147 can be readily determined. Of course, radiopaque markers can also be used as desired with any of the embodiments. It should further be noted that the tubular member 147 should be flexible enough to readily navigate the necessary vascular passages as it moves along the guidewire 140 and the member 147 may also be of a predetermined non-linear shape.

Figure 19:
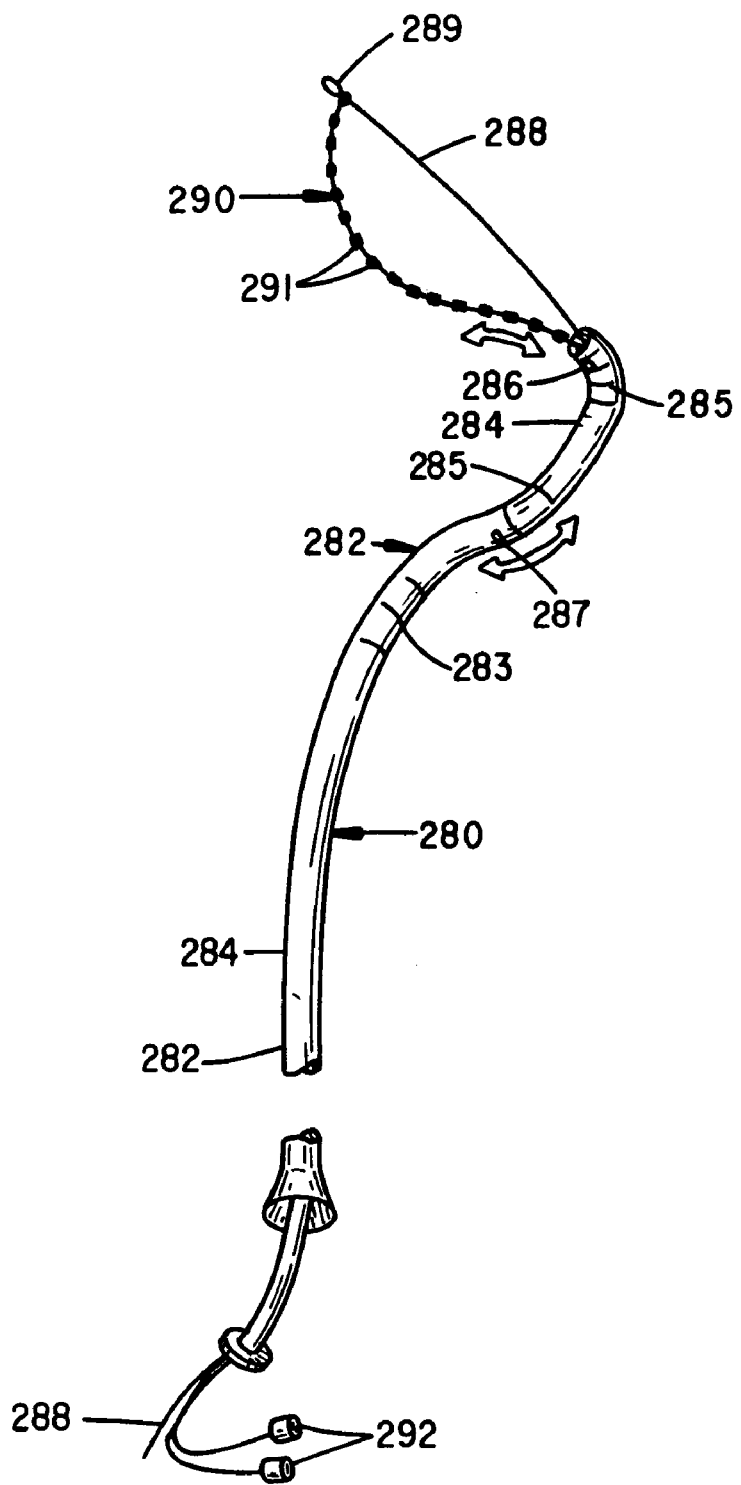
FIG. 19 is a schematic view of still another embodiment of a catheter in accordance with the invention.

FIG. 19 represents a rudimentary schematic view of yet another catheter embodiment generally at 280 illustrating the use of a double concentric directional deflection sheath system in such a device. Directional deflective sheath systems are sheaths which utilize one or more relatively weak or more flexible wall areas aligned in the same or radially diverse directions serially spaced for producing greater flexibility in a preferred direction in the outer wall of the sheath. Thus, a plurality of directional flexure tendencies may be consecutively induced in a single sheath or in concentric super-imposed sheaths which overlap and combine to modulate the total bending characteristics. Either such system is contemplated for the catheters of the present invention and the system illustrated at 280 in FIG. 19 is one using a double sheath layer. The double directed sheath system includes an outer directional tubular sheath 282 overlaying an inner directional sheath 284 shown with respective directional notches 283 and 285.

The directional notches are indicative of but one of a number of ways to impart the weakness or increased flexibility to the sheath in a particular direction. Direction control members or filaments threaded through the sheath system are normally attached to the internal sheath surface or wall as at 286 and 287 to control the deflection of the weakened section just proximal of the attached control member. Other techniques include directionally weakened wall sections, directionally weakened wall sections used in cooperation with internal flexure control members and the use of internal flexure control members alone. These systems are used in conjunction with axially adjustable control filaments or wires fixed to the sheath distal of the weakened area sought to be controlled. Greater details concerning directional sheath systems including configurations and directional controls for them can be found in applicant's copending application Ser. No. 08/148,598, filed Nov. 8, 1993, now U.S. Pat. No. 5,441,483, issued Aug. 15, 1995, entitled "CATHETER DEFLECTION CONTROL", which itself is a continuation-in-part of Ser. No. 07/976,784, filed Nov. 16, 1992, abandoned, which are hereby incorporated herein by reference in their entirety for any necessary purpose.

The outer sheath may be axially adjustable relative to the inner sheath and generally will possess a different preferred directional orientation or tendency to deflect in a different direction. Interaction between the concentric sheath layers can be used to adjust the relaxed or controlled shape of the distal portion of the sheath system just proximal the working catheter section as shown generally at 286. A guidewire is depicted at 288 with stopper ball 289 and the electroded working catheter section is shown including electrodes 291 on deployed portion 290. Electrical leads are depicted at 292.

It is further apparent that the use of a deflection controlled sheath member or combination of diversely orientated direction controlled sheath members represents another important way to impart additional precision to the control of the navigation and shape of the electroded working catheter to facilitate proper placement of the electrode system of many of the embodiments disclosed. The actual deflection of such member, of course, can be modulated or controlled by any of many techniques such as those illustrated in the above incorporated references. Thus, axially displaceable control elements may be fixed to each active deflection sheath member below the directional deflection portion to control deflection with or without auxiliary internal deflection member, for example.

Figure 22A:
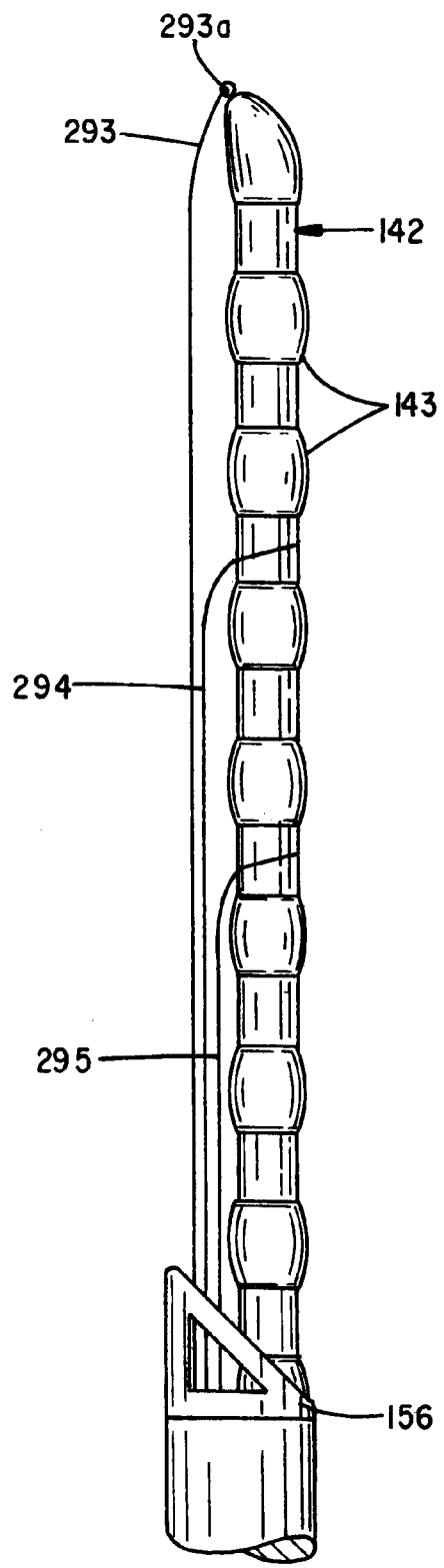
FIGS. 22a–22c depict another embodiment in which a working catheter system is provided with an alternate multi-element control system.
Figure 22C:
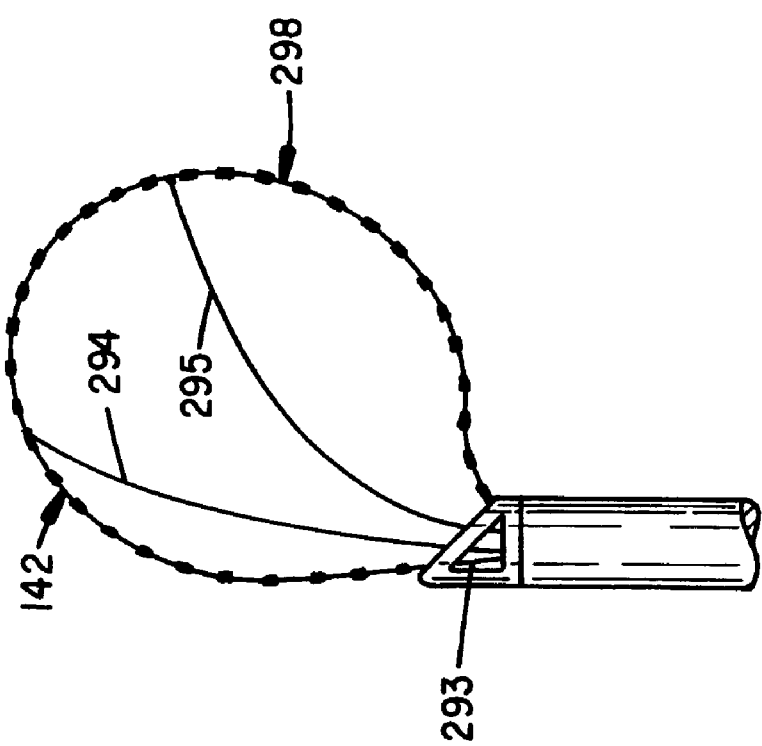
Figure 22B:
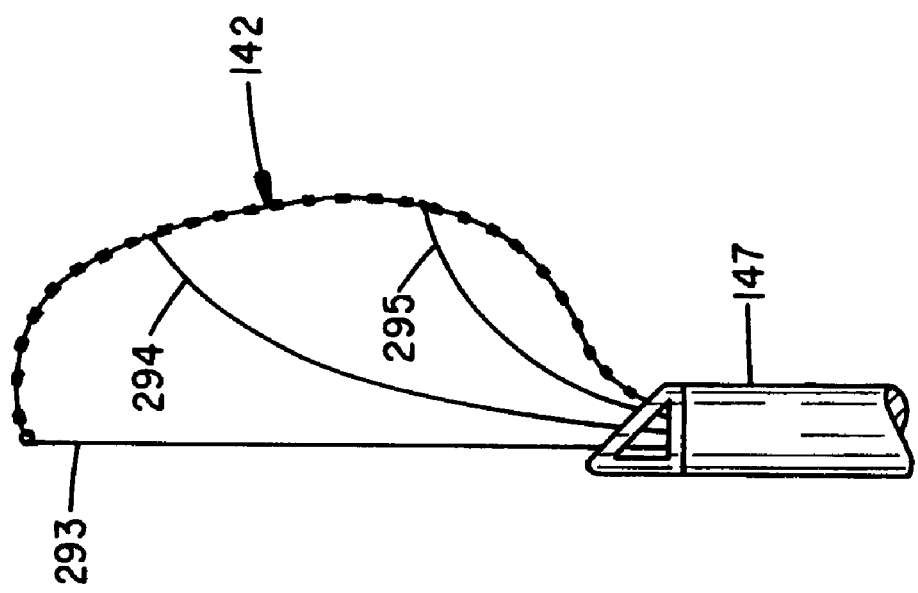

Additional alternate control or shape modifying systems are depicted in FIGS. 22a–22c. In FIG. 22a, an electroded spine or catheter similar to ones previously shown in conjunction with FIGS. 18a and 18b, for example, has a modified distal extremity fitted with a non-conductive and relatively rigid distal control member or element 293 fixed to the distal end at 293a and additional non-conductive, relatively rigid control elements 294, 295 are attached between electrodes spaced proximally along the electroded member 142 as at 196 and 197, respectively. The mode of attachment of the control members 294 and 295 is such that the member 142 is free to turn relative to the attached control elements. The elements 293, 294 and 295 cooperate in axial adjustment as shown in FIGS. 22b and 22c in more schematic form to control curvature of the member 142 even to produce a controlled loop configuration at 298 in FIG. 22c. Of course, the control members 294 and 295 must have sufficient tensile to avoid collapse of the loop 298 which may attempt to straighten to reassume shape of FIG. 22a.

Figure 23:
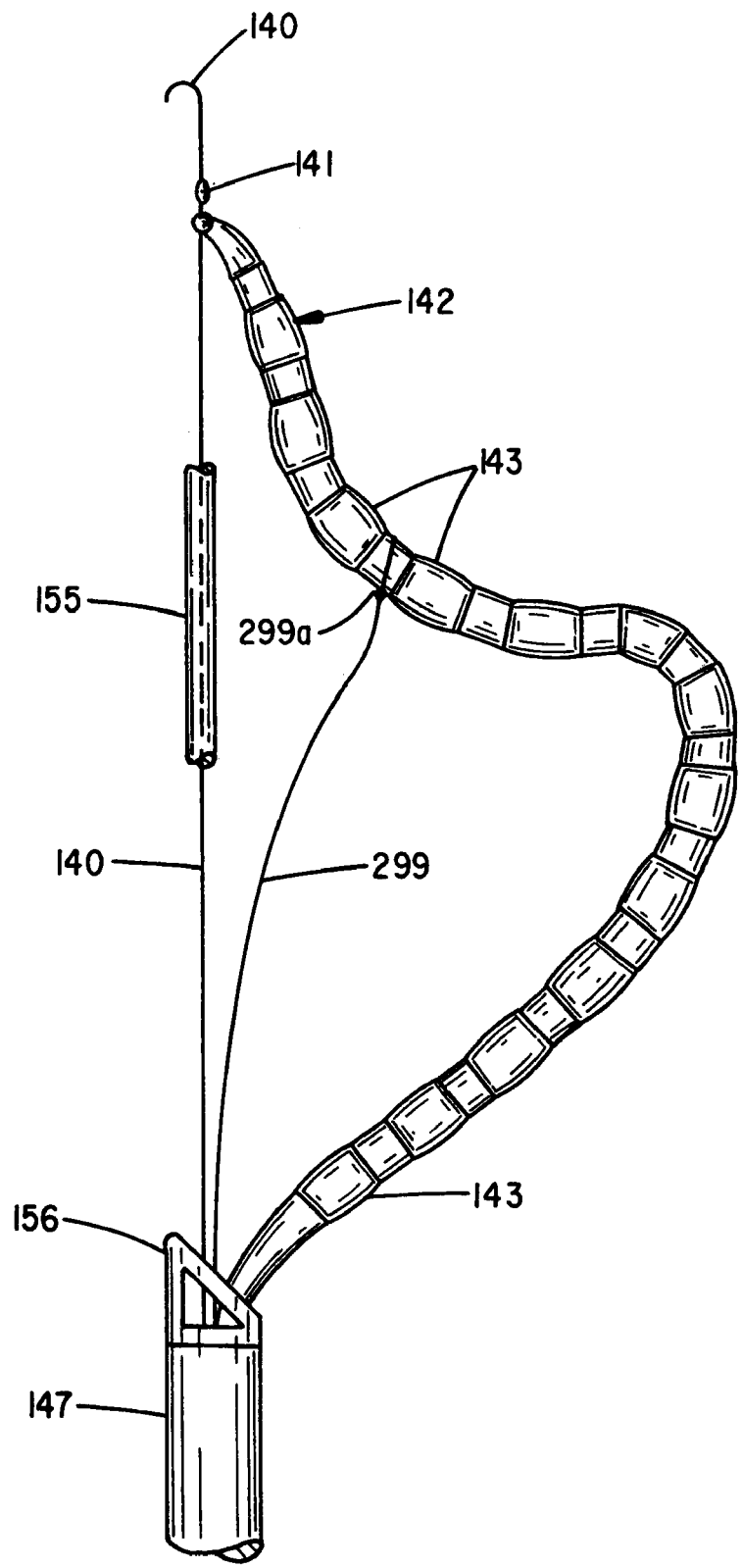
FIG. 23 depicts yet another embodiment in which a system similar to FIG. 8, 18a or 18b is provided with additional control member.

In FIG. 23, an embodiment similar to either FIG. 18a or 18b is provided with an intermediate control element 299 attached to the catheter or spine 142 at 299a in the manner of those previously discussed in conjunction with FIGS. 22a–22c, above. The element 299, which may be a nonconducting, relatively rigid control wire or the like, can be tensioned to adjust the shape of the catheter 142 as necessary intermediate the guide member eye and the sheath opening. The member 142 resists the modification as it attempts to resume the arcuate configuration of FIGS. 18a and 18b. Additional spaced intermediate elements can be used if desired.

Figure 20:
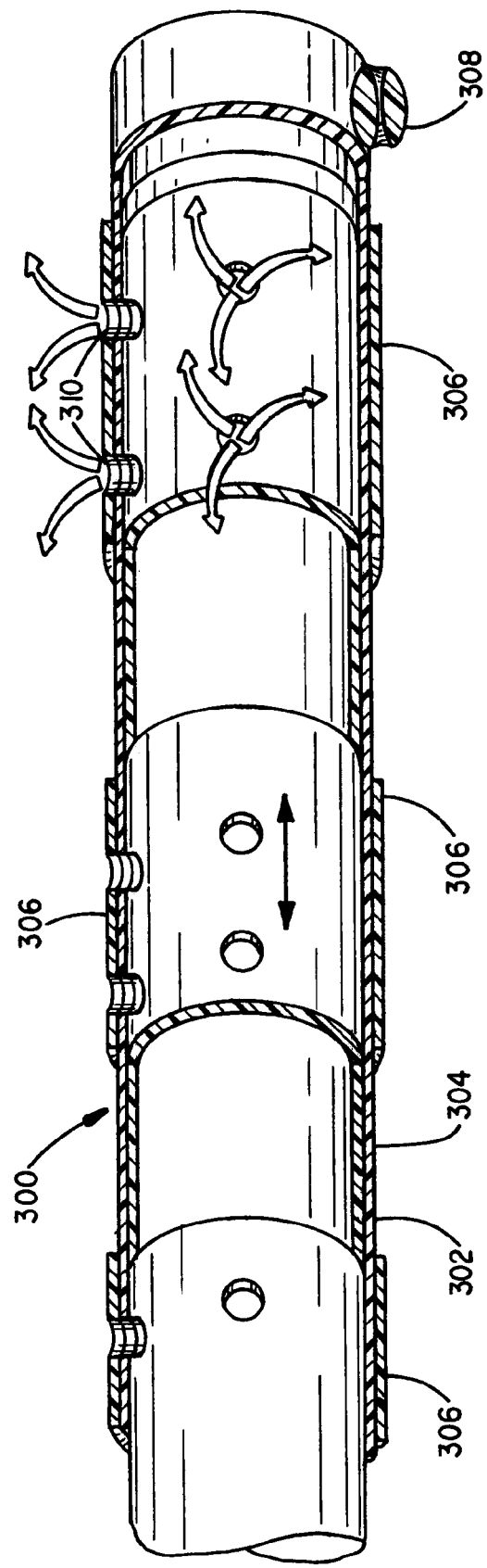
FIG. 20 depicts a greatly magnified fragmentary view of the distal end of a working catheter segment in accordance with the invention showing the water effusion system.

The deployment and shape control techniques associated with the catheters of the invention including the possible use of active deflection sheaths all assisting in the control of various catheter embodiments. FIG. 20 depicts a greatly enlarged schematic view of a distal fragment of a working catheter section at 300 illustrating an auxiliary cooling system for use in ablation as can be used with any of the catheters but is particularly illustrated with a catheter such as shown in FIGS. 8, 18a and 18b. The catheter is provided with a system that includes an inner sliding tubular member 302 operable, within the outer tubular catheter member 304. A series of spaced ring or hollow bead electrodes are shown that encircle the outer catheter 304 at 306, a rider or guidewire eye is shown at 308. The electrodes 306, normally metallic, are further provided with axially spaced series of radially spaced pores or effusion openings 310 aligned with congruent or similar openings in the catheter member 304 to which they are fixed. The tubular member 302 is also provided with effusion openings or pores that can be aligned with the openings 310. The inner tube 302 is configured to slide and rotate within the member 304 in a manner that enables the effusion openings to be aligned or misaligned such that coolant fluid supplied to the inner tubular member 302 can be effused to cool or withheld from the electrodes 306 by the relative position of the member 302.

Figure 21:
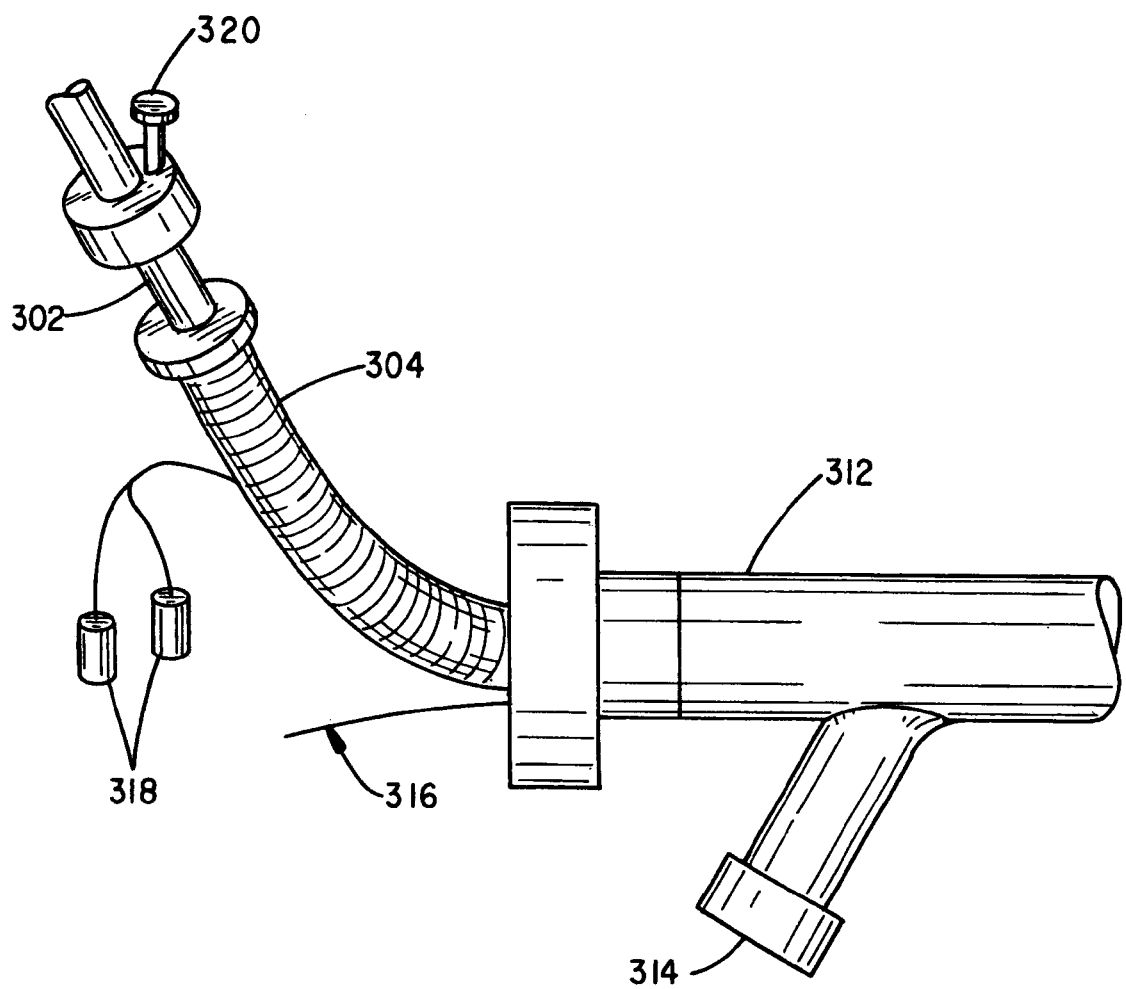
FIG. 21 is a view in slightly reduced scale of the proximal terminal portion of the catheter of FIG. 20.

FIG. 21 depicts a typical proximal fragment to be used with the distal fragment of FIG. 20 and includes a sheath with an infusion port 314 for infusing washing saline or other material to the member 304 and sheath. A guidewire is shown at 316 with electrical leads 318. The inner coolant tube 302 is provided with an infusion port for saline or other benign coolant material at 320.

The size and number of the openings or pores 310 may vary but generally a 7 French electrode about 4 mm in length will be provided with about 4–8 openings having a nominal diameter between 0.2 and 0.6 mm, nominally 0.4 mm. This system helps to control the temperature as necessary at the ablation sites. Thermocouple or other temperature monitoring techniques may be employed in a well-known manner to monitor the electrode temperature if desired.

Figure 28:
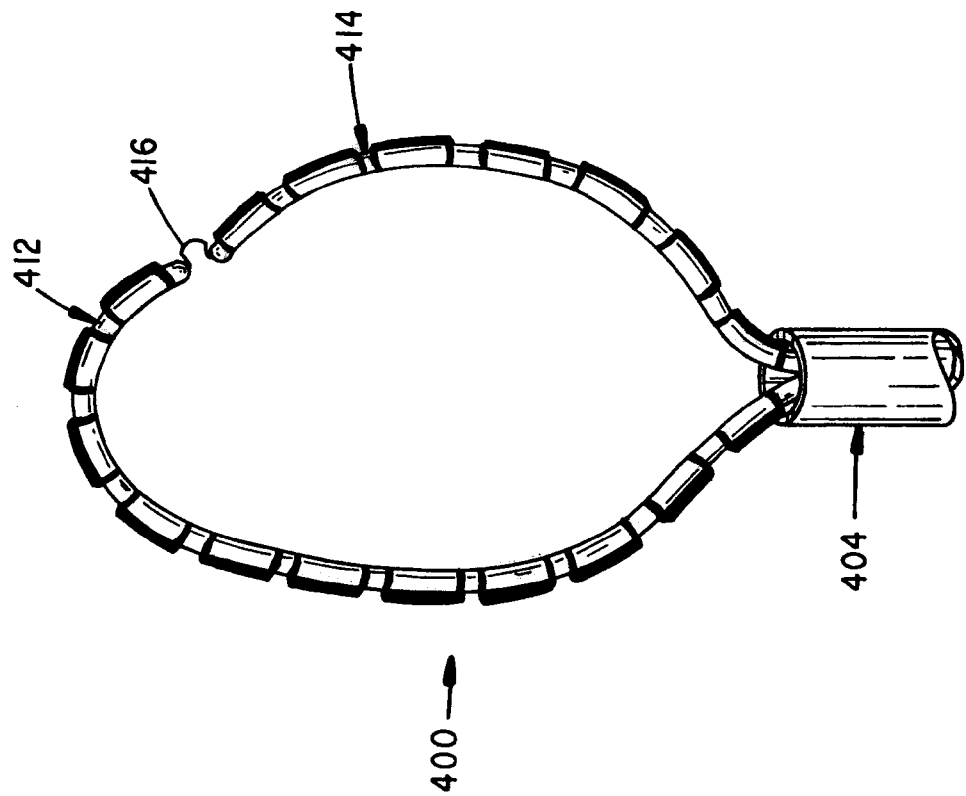
FIG. 28 depicts an asymmetrical loop ribbon configuration.

The mapping and ablation system of the invention may also take on a ribbon like loop configuration. Embodiments of this category are depicted in FIGS. 24–30. A mapping and ablation ribbon device shown generaly at 400 is nominally deployed from a distal end opening 402 of a main steerable vascular catheter or sheath 404 and is shown at least partially deployed in the figures. The ribbon 400 is held in a generally collapsed loop state in the sheath with two individually deployable and controllable loop segments 406, 408 nested in substantially parallel back to back relation (FIG. 25) joined by a high strength flexible bridge member 410. This embodiment is shown in a symmetrical loop expanded disposition in FIG. 27. An asymmetric arrangement in which the two segments are deployed unequally as shown in the view of FIG. 28 in which a major segment 412 is joined to a minor segment 414 by a flexible bridge at 416. Still another version of the ribbon system is depicted in the perspective fragmentary views of FIG. 29 and FIG. 30 in which a ribbon 418 is deployed with the bridge segment 420 at the point of emergence at the distal end of the sheath 404. This sheath is one having a plurality of adjustable sheath rings 426 and one or more deflection control wires as at 427 attached to the sheath at 428 to control deflection as previously described. This represents a totally asymmetric arrangement. Of course, symmetry can be controlled by relative extension of each of the emerging loop segments.

The ribbon catheter system like those previously described carries a serially mounted electrode array consisting of a plurality of serially arranged electrodes 422 each connected by an isolated insulated conductive connector or filament as at 424. The system is configured in a manner such as has been described so that each electrode is capable of registering an electrical signal individually for mapping and can be energized individually as in any desired combination with other of the electrodes of the catheter to accomplish spot or linear ablation. Linear lesions can be induced in any orientation in any chamber by proper orientation of the sheath and loop combination.

Figure 26:
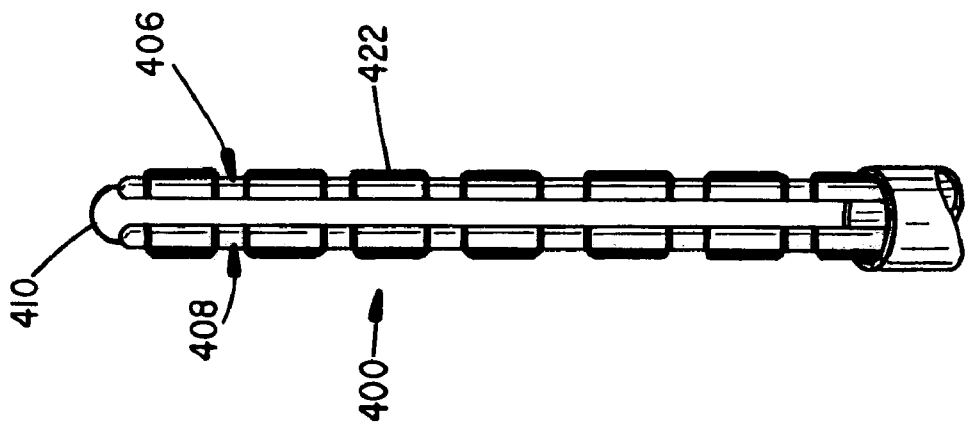
FIG. 26 is an enlarged fragment of a ribbon catheter section illustrating types of electrodes suitable for use in various versions of the several embodiments of ribbon catheters in accordance with the invention.
Figure 25:
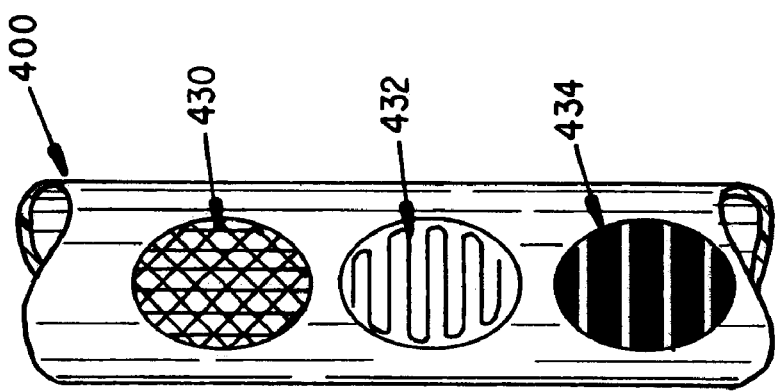
FIG. 25 is a view of the ribbon catheter of FIG. 24 rotated 90° to show the collapsed or stored profile.
Figure 24:
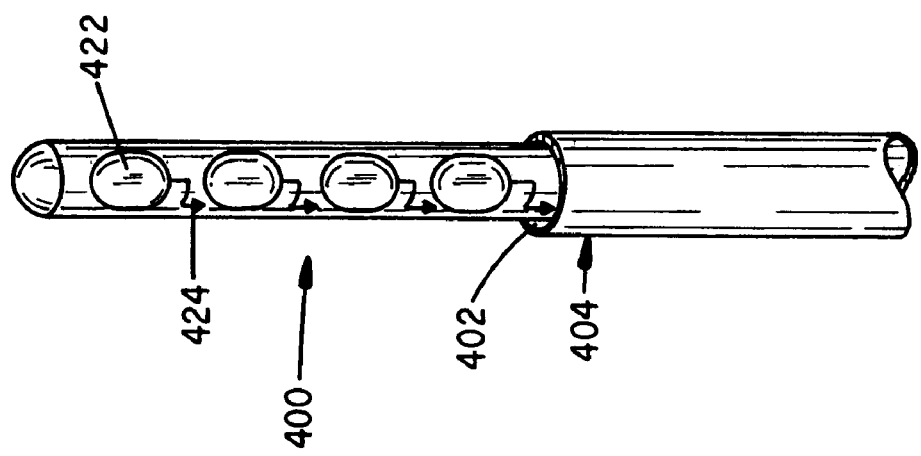
FIG. 24 is an enlarged side view of a ribbon type mapping and ablation device in accordance with the invention emerging from the distal end of an outer sheath.
Figure 27:
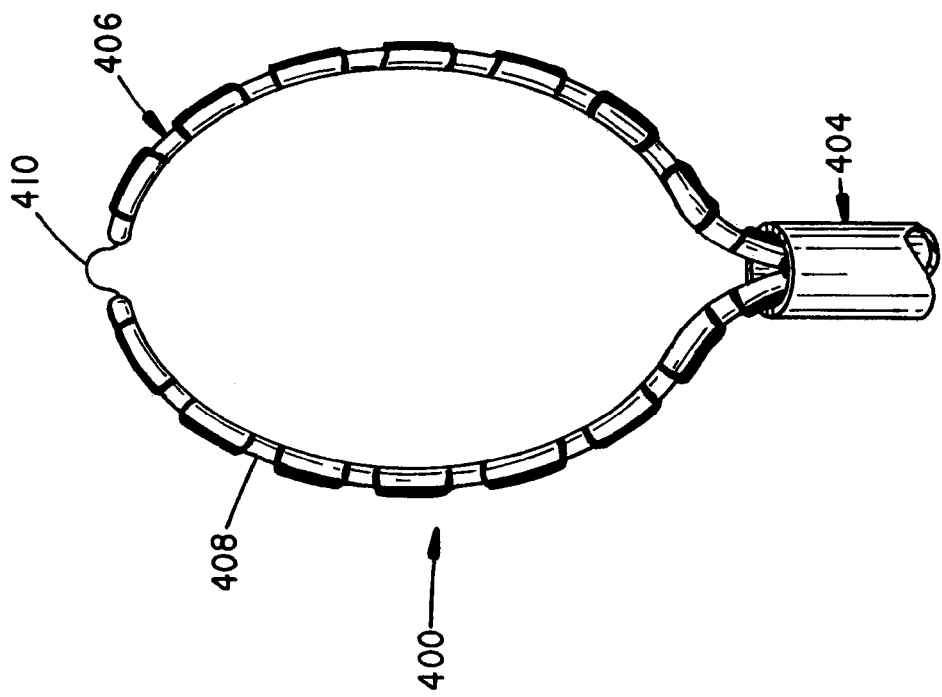
FIG. 27 shows the ribbon mapping and ablation device deployed as a symmetrical loop configuration.
Figure 29:
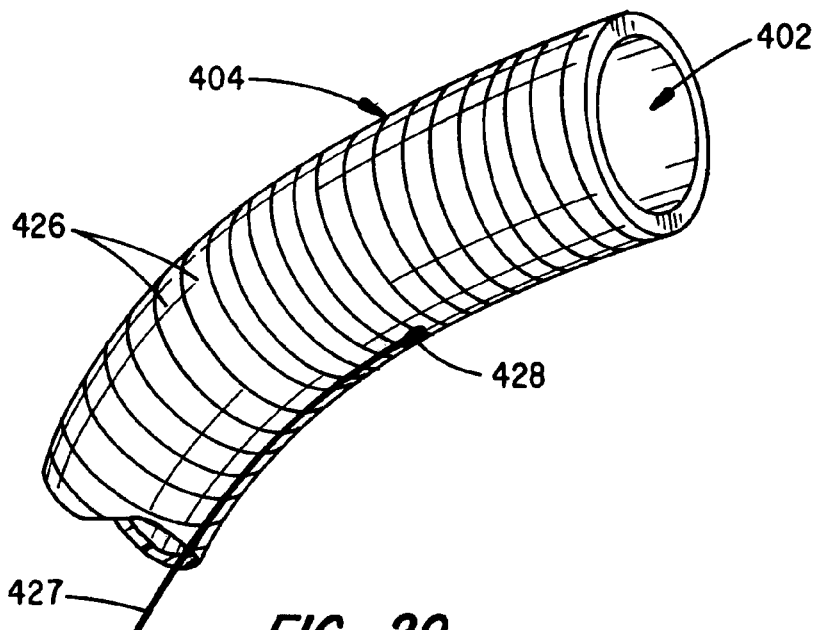
FIGS. 29 and 30 depict a steerable catheter sheath and the sheath with a ribbon mapping and ablation device deployed therefrom.
Figure 30:
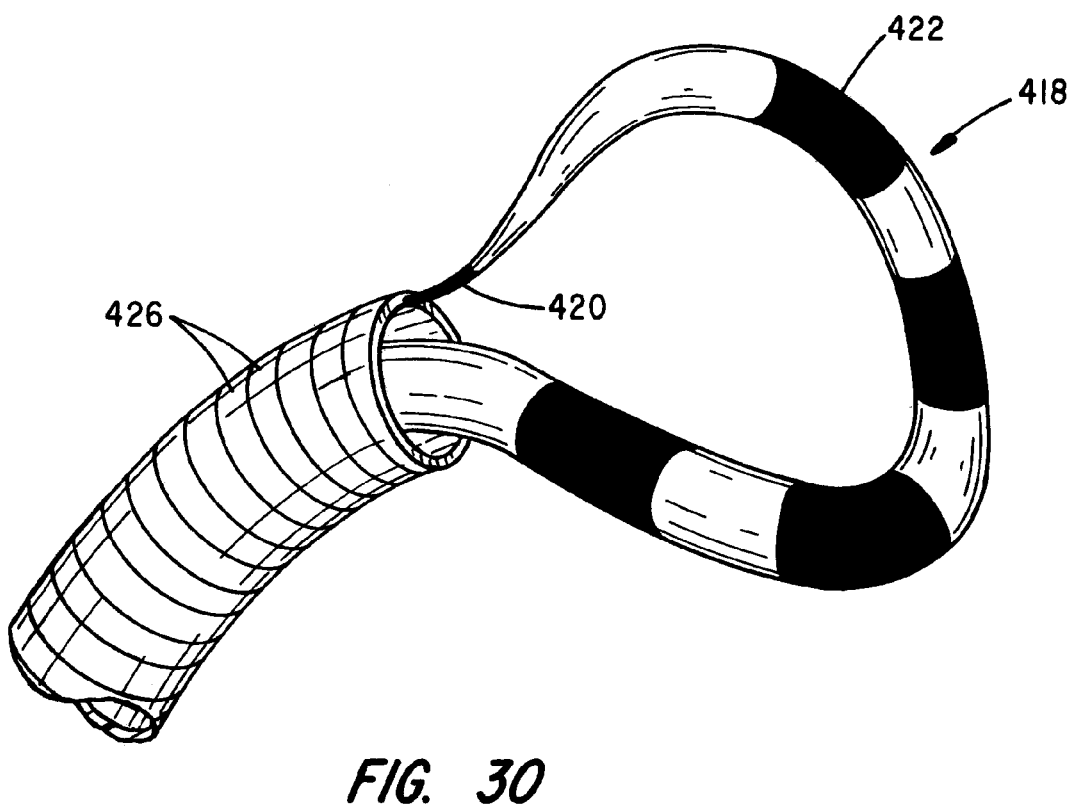

With respect to the electrodes themselves, particularly as pictured in FIGS. 25, 27 and 28 they may be areas of any desired size slightly raising above the outer surfaces of the ribbon. Examples of electrodes are shown in FIG. 26. For example, the electrodes may be as thin as a deposited film or conductive paint material as at 430, may be configured from a strand of conductive wire packed in convoluted switch back loops as depicted at 432 or may be in the form of a segmented conductive pattern as shown at 434. Other types compatible with the ribbon catheter contruction will occur to the skilled artisan. Typically raised electrodes are in the order of about 0.5 mm thick and 4–5 mm long by 2.5 to 3 mm wide. The inter-electrode distance also may vary but is typically less than the electrode length so that energizing consecutive electrodes produces continuous linear lesions.

It is further contemplated with respect to certain control wire or guidewire mounted catheter systems in accordance with the invention to add a further degree of control with respect to the relative rotational or angular displacement between the wire and the distal rider or guidewire eye. The ability to control or fix the distal end with respect to a particular orientation about the guidewire in a system having an over the wire distal tip construction enables better control of orientation during deployment for a mapping and ablation procedure.

A series of embodiments illustrating tip and wire locking mechanisms are shown in FIGS. 31–34. FIGS. 31 and 31a depict a ball and socket type system in which a locking ball member 440 is attached to the guidewire 442 at the lower end of a floppy tip 444 the guidewire eye 446 of the catheter 448 contains an upper or distal recess 450 designed to accommodate locking ball 440 as the wire 442 is withdrawn through the guidewire eye. In FIG. 32 a slot 462 in the tip of catheter 460 is used in combination with a key 464 fixed to central guidewire 466 having floppy tip 468. FIGS. 33a and 33b depict another embodiment in which a catheter 470 with offset guidewire eye 472 is slidably engaged on guidewire 474 which in turn is provided with a fixed shaped locking clip 476 which locks against a catheter nose shape at 478 when the wire 474 is retracted. A floppy guide tip is shown t 479. FIG. 34 depicts a distal catheter tip fragment 480 with guidewire eye 482 threaded over guidewire 484. The guidewire eye is of a rectangular shape to accommodate a similary shaped key member 486 fixed to wire 464 just proximal soft tip 488. Of course, any desired polygon key shape can be used.

Figure 35:
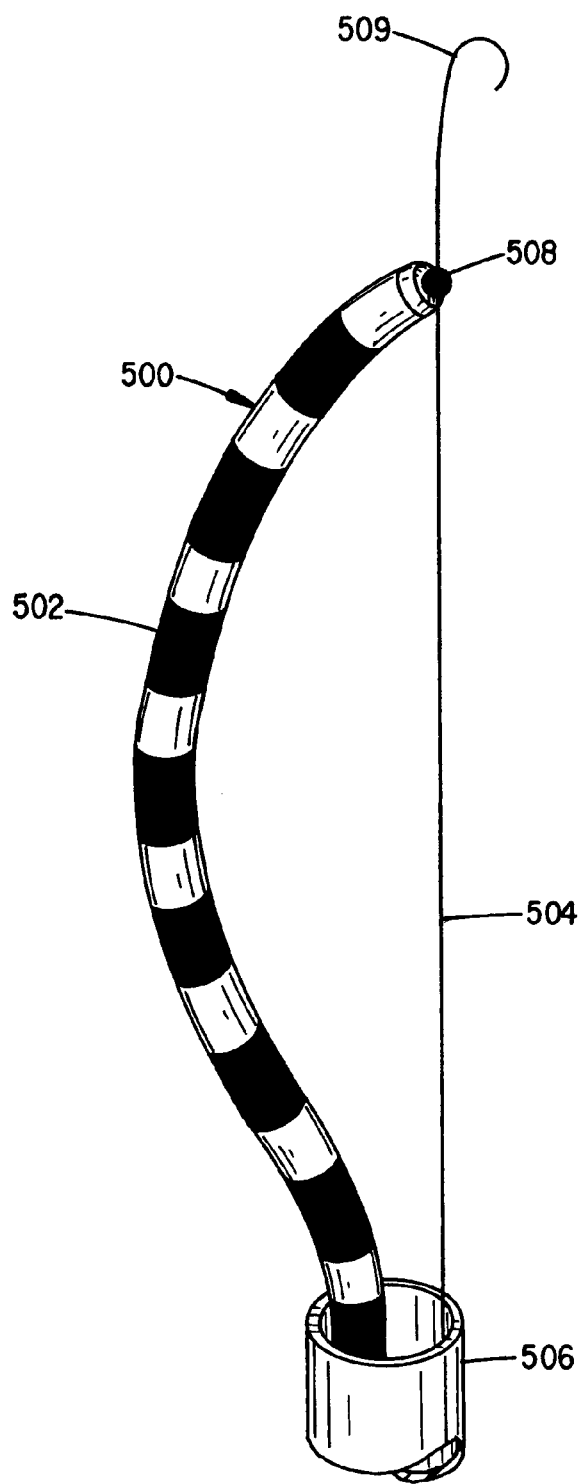
FIG. 35 depicts a deployed catheter having a distal tip fixed to a guidewire having a floppy distal soft tip guide hook.
Figure 36:
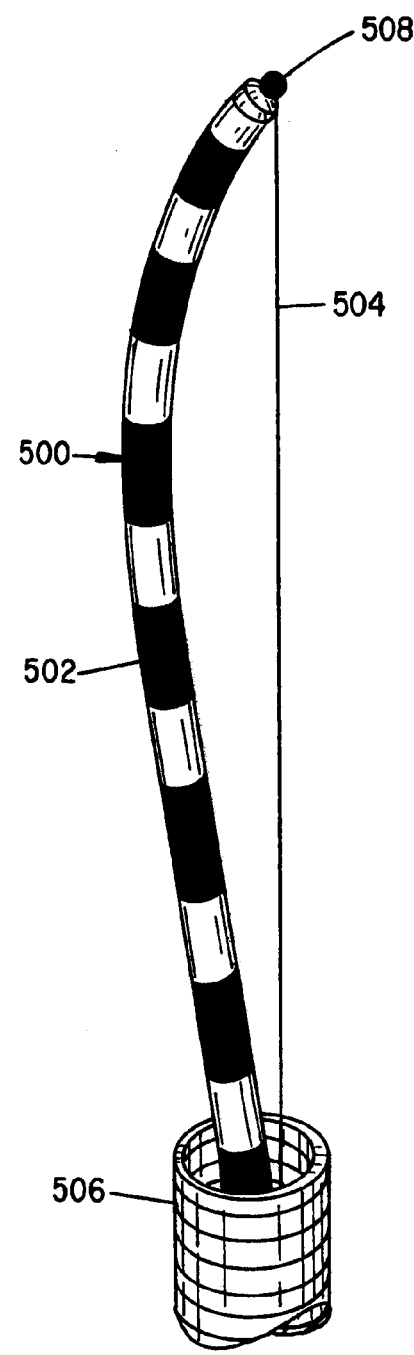
FIG. 36 is a view of an embodiment similar to that of FIG. 35 without the guide tip.
Figure 37:
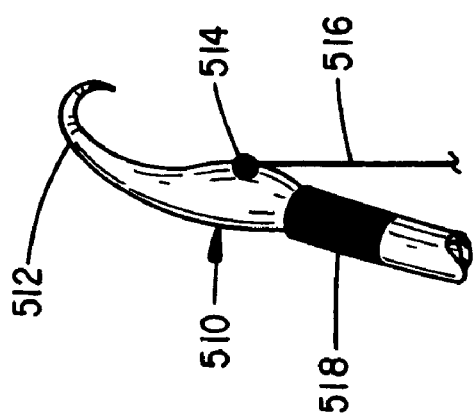
FIG. 37 shows an alternative self-guiding and anchoring catheter tip.

Another control technique involves fixing the distal end of the catheter to a control wire or element. This is illustrated in the fragmentary views of FIGS. 35–37. In FIG. 35, a mapping and ablation catheter 500 carrying electrodes 502 is shown emerging with a control wire 504 from a sheath 506. The distal end of the catheter 500 is permanently connected to the wire 504 at 508 just proximal pigtail 509. FIG. 36 shows the catheter of FIG. 36 sans pigtail 509. FIG. 37 depicts the distal tip fragment of a similar catheter 510 in which the tip 512 is formed into a guiding and anchoring hook above a permanent attachment point 514 of an associated control wire 516 just above a distal ring electrode shown at 518.

Figure 38:
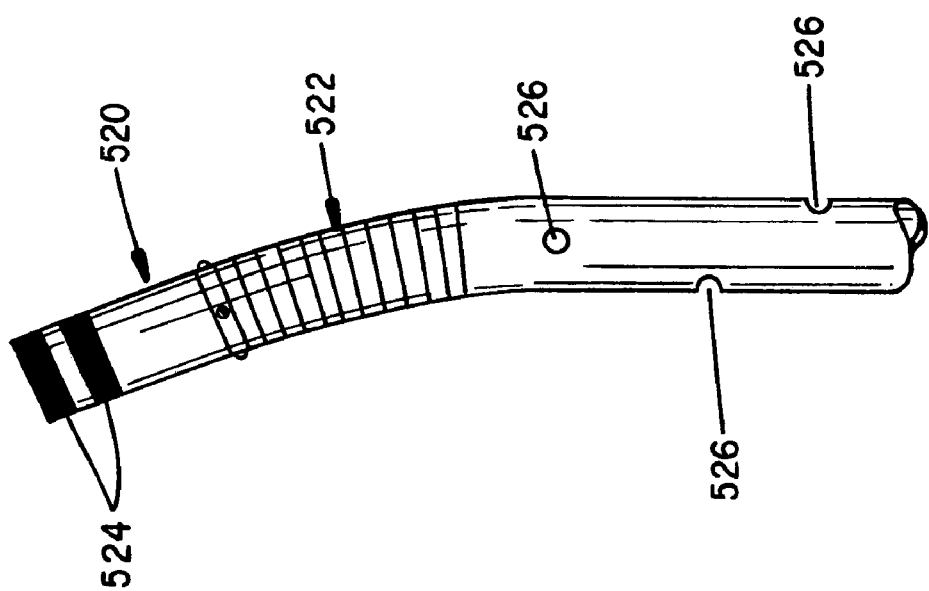
FIG. 38 depicts a catheter sheath having distal air release openings.

FIG. 38 depicts a sheath, generally 520, for containing a catheter or other recorded and ablation system such as those previously described. This system is particularly useful in addressing the left heart chambers via the right heart chambers. It has a deflectable are a 522 and a plurality of distal position recording and x-ray enhancing or locator rings at 524 for locating the distal end of the sheath. The sheath is also provided with one or more vent openings 526 which are designed to allow air to be released at a point sufficiently proximal to the distal end such that the vent openings remain in the right heart area when the left heart area is addressed by a mapping and ablation device eminating from the distal end. In this manner air released from the sheath volume will be safely exchanged in the lungs prior to the blood entering the left atrium. The system is designed to contain a catheter or other recording and ablation device which can be deployed from the distal end of the sheath.

This invention has been described herein in considerable detail in order to comply with the Patent Statutes and to provide those skilled in the art with the information needed to apply the novel principles and to construct and use embodiments of the example as required. However, it is to be understood that the invention can be carried out by specifically different devices and that various modifications can be accomplished without departing from the scope of the invention itself.

I claim:

1. A recording and ablation system for mapping electrical activity and creating ablation lesions in a cardia chamber of interest comprising:

(a) a hollow outer catheter or sheath;

(b) an inner catheter member operable within said outer catheter or sheath and including a flexible distal recording and ablation device extendable to protrude from a distal opening in said outer catheter or sheath, said recording and ablation device being axially adjustable relative to said sheath and having a distal tip;

(c) a control system including one or more control elements connected to said inner catheter member, said one or more control elements being axially adjustable relative to said sheath to assist and enable control of the geometric shape assumed by said flexible distal recording and ablation device when protruding from an opening in said outer catheter or sheath;

(d) wherein said one or more control elements connected to said inner catheter member include a control member connected at or near the distal tip of said inner catheter member;

(e) wherein said flexible distal recording and ablation device comprises a plurality of serially spaced, electrically isolated, separately connected electrodes in combination forming a continuous array;

(f) a circuit system enabling separate signal reception for mapping and separate energization to accomplish spot and linear ablation; and (g) a guide member associated with the deployment of said inner catheter member.

2. The apparatus as in claim 1 wherein the guide member is formed as a continuation of the distal tip of said inner catheter member.

3. The apparatus as in claim 1 wherein said guide member is formed as the distal tip of one of said one or more control elements which is associated with the distal tip of said inner catheter member.

4. The apparatus as in claim 3 wherein one of said one or more control elements is fixed near the distal tip of said inner catheter member.

5. The apparatus as in claim 3 wherein one of said one or more control elements is movable relative to said inner catheter member.

6. The apparatus as in claim 5 including a locking mechanism for preventing relative rotation between one of said one or more control elements and said inner catheter member.

7. The apparatus as in claim 1 wherein said one or more control elements comprise a plurality of control elements and including an element connected at or near the distal tip of said inner catheter member and additional elements connected at points spaced from said distal tip of said inner catheter member.

8. The apparatus as in claim 7 wherein each said control element comprises an axially adjustable control wire.

9. The apparatus as in claim 1 wherein one of said one or more control elements comprise an axially adjustable control wire.

10. The apparatus as in claim 9 wherein each one of said one or more control elements is fixed to said inner catheter member.

11. The apparatus as in claim 1 further comprising a system to supply infusion cooling fluid to said inner catheter member.

\* \* \* \* \*